(12) United States Patent
Bovin et al.

(10) Patent No.: US 12,187,817 B2
(45) Date of Patent: Jan. 7, 2025

(54) PREPARATION OF CERAMIDE CONJUGATES AND DERIVATIVES OF SPHINGOLIPID ANALOGUES

(71) Applicant: KODE BIOTECH LIMITED, Auckland (NZ)

(72) Inventors: Nicolai Vladimirovich Bovin, Moscow (RU); Stephen Micheal Henry, Auckland (NZ); Alexander Borisovich Tuzikov, Moscow (RU)

(73) Assignee: KODE BIOTECH LIMITED, Auckland (NZ)

( * ) Notice: Subject to any disclaimer, the term of this patent is extended or adjusted under 35 U.S.C. 154(b) by 0 days.

(21) Appl. No.: 18/363,810

(22) Filed: Aug. 2, 2023

(65) Prior Publication Data

US 2023/0374076 A1 Nov. 23, 2023

Related U.S. Application Data

(62) Division of application No. 15/734,100, filed as application No. PCT/IB2018/053967 on Jun. 4, 2018, now Pat. No. 11,760,779.

(30) Foreign Application Priority Data

Jun. 2, 2017 (AU) ................. 2017902104
Jun. 2, 2017 (AU) ................. 2017902105

(51) Int. Cl.
| C07K 9/00 | (2006.01) |
| A61K 47/54 | (2017.01) |
| A61K 47/64 | (2017.01) |
| C07K 1/107 | (2006.01) |
| C07K 19/00 | (2006.01) |

(52) U.S. Cl.
CPC ............ *C07K 9/001* (2013.01); *A61K 47/545* (2017.08); *A61K 47/549* (2017.08); *A61K 47/64* (2017.08); *C07K 1/1077* (2013.01); *C07K 19/00* (2013.01)

(58) Field of Classification Search
None
See application file for complete search history.

(56) References Cited

FOREIGN PATENT DOCUMENTS

| WO | WO-2009048343 A1 * | 4/2009 | ........... A61K 47/544 |
| WO | 2015/015496 A1 | 2/2015 | |
| WO | 2016/080850 A1 | 5/2016 | |

OTHER PUBLICATIONS

International Search Report for PCT/IB2018/053967, mailed Aug. 16, 2018, 6 pages.
Written Opinion of the ISA for PCT/IB2018/053967, mailed Aug. 16, 2018, 6 pages.
International Preliminary Report on Patentability for PCT/IB2018/053967, completed Apr. 18, 2019, 4 pages.
Taguchi et al., "Sphingomyelin analogues as inhibitors of sphingomyelinase", Biorganic & Medicinal Chemistry Letters, 2003, vol. 13, pp. 1963-1966.
Henry et al., "Rapid one-step biotinylation of biological and non-biological surfaces", Scientific Reports, published Feb. 12, 2018, 48 pages.
Ong et al. (Synthesis of ceramides using N-hydroxysuccinimide esters, Journal of Lipid Research 13(1972) 819-822) (Year: 1972).

* cited by examiner

*Primary Examiner* — Christina Bradley
(74) *Attorney, Agent, or Firm* — NIXON & VANDERHYE

(57) ABSTRACT

The preparation of water dispersible ceramide conjugates and derivatives of sphingolipid analogues is described. The conjugates and analogues are prepared by reacting a succinimidyl carbonate of a β-Ala derivative with the primary amine of a functionalised spacer. Despite their dispersibility in water, the ceramide conjugates and derivatives of sphingolipid analogues spontaneously incorporate in to the plasma membranes of cells.

5 Claims, 6 Drawing Sheets

A

B

PREPARATION OF CERAMIDE CONJUGATES AND DERIVATIVES OF SPHINGOLIPID ANALOGUES

CROSS REFERENCE TO RELATED APPLICATIONS

This application is a Divisional of application Ser. No. 15/734,100, filed on Dec. 1, 2020, which is the National Phase under 35 U.S.C. § 371 of International Application No. PCT/IB2018/053967, filed on Jun. 4, 2018, which claims the benefit under 35 U.S.C. § 119(a) to Patent Application Nos. 2017902105, filed in Australia on Jun. 2, 2017 and 2017902104, filed in Australia on Jun. 2, 2017, all of which are hereby expressly incorporated by reference into the present application.

TECHNICAL FIELD

The invention relates to biomimetic ceramide conjugates and derivatives of 2-(tetradecyl)hexadecanyl and its homologues. The functionalised conjugates and derivatives are dispersible in water yet spontaneously incorporate into the plasma membranes of cells.

BACKGROUND ART

Sphingolipids are a group of acyl lipids based on the $C_{18}$ long chain amino alcohol sphingosine (D-erythro-2-amino-trans-4-octadecene-1,3-diol). Sphingolipids are generally located in the outer leaflet of the plasma membrane. The group includes both glycolipids and phospholipids.

Both the amino and the hydroxy groups of sphingosine may be substituted. Acylation of the amino group yields a ceramide with an amide bond that is resistant to alkaline hydrolysis. The simplest glycosphingolipids are the mono-glycosyl ceramides or cerebrosides. Gangliosides contain one or more sialic acid residues linked to the sugar residues of a glycosphingolipid.

In vivo the de novo synthesis of ceramides begins with the condensation of palmitate and serine to form 3-keto-dihydrosphingosine. The product of this condensation is then reduced to dihydrosphingosine followed by acylation to form the amide bond containing dihydroceramide. Desaturation of this intermediate yields ceramide.

In addition to their structural role sphingolipids, such as ceramide, can participate in cellular signalling regulating differentiation, apoptosis and autophagy of cells. The synthesis of glycosphingolipid analogues comprising a 2-branched fatty alkyl residue in place of ceramide is well established. The non-structural activities of some of these glycosphingolipid analogues have also been identified.

The publication of Choi et al (1996) discloses the preparation of polyethylene glycol modified ceramide lipids. The lipids are used to form liposomes that may contain anti-cancer agents.

The publication of Galili (2010) discloses that an intratumoural injection of glycosphingolipids with α-Gal epitope results in tumour regression and/or destruction. Binding of the natural anti-Gal antibody to de novo expressed tumoural α-Gal epitopes induces inflammation and activation of tumour specific T cells.

The publications of Hasegawa et al (1995), Ohmoto et al (1996) and Wada et al (1996) disclose the preparation and evaluation as selectin blockers of a range of sialyl Lewis X analogues. Glycosylation of 2-tetradecylhexadecan-1-ol yielded a more potent selectin blocker with broad inhibitory activities towards E-, P- and L-selectins. The conjugate was presented as a potential therapeutic for inflammatory disorders.

The publication of Kiso and Hideharu (2003) discloses carboxymethylgalactose derivatives including derivatives where the carboxymethylgalactose moiety is conjugated directly or indirectly (via a disaccharide) to 2-(tetradecyl)-1-hexadecanol. The derivatives are asserted to be useful in treating and preventing various selectin-related diseases such as inflammations and cancerous metastasis.

The publication of Fuse et al (2006) discloses the synthesis of GM to analogues in which the GM to epitope is coupled to a variety of 2-(tetradecyl)hexadecanyl glycosides. The analogues were synthesized in the context of investigations into the susceptibility of the GM to ganglioside to enzymatic hydrolysis.

The publication of Hada et al (2007) discloses synthetic analogues of a novel glycosphingolipid isolated from the marine sponge Aplysilla rex. A glycolipid analogue carrying a 2-branched fatty alkyl residue in place of ceramide was synthesized. Among a range of glycolipid analogues that were synthesized this analogue showed the most potent nitric oxide (NO) production inhibitory activity against LPS-activated J774.1.

The publication of Yoon et al (2007) discloses the synthesis of ceramide mimetic conjugates where N-linked oligosaccharides are conjugated to "aminoceramide" (2-(tetradecyl)hexadecamine). The conjugates were synthesized in the context of investigations into self-recognition attributed to carbohydrate-to-carbohydrate interactions (CCI) and autoaggregation of cells. For these investigations the ceramide mimetic conjugates were found to bind more strongly than phosphatidylethanolamine conjugates to polystyrene plates when incorporated into liposomes.

The publication of Compton et al (2014) discloses derivatives of glycan sphingolipids. The publication discloses findings that in the synthesis of α-galactosyl ceramide the hydrogenolytic deprotection of a specified compound with $Pd(OH)_2$ leads to the isolation of significant quantities of an amine by-product designated CN089. It is asserted that derivatives of the amine by-product where O to N acyl migration is blocked may be useful products.

The publication of Anderson et al (2015) discloses peptidylated aminoglycan ceramides for use in the targeting in vivo of the CD1 protein of natural killer T-cells (NKT cells). These compounds are provided with a self-immoliative linker group between the peptidyl moiety and the aminoglycan ceramide moiety. Examples of these compounds are asserted to induce an increased antigen-specific T-cell response as compared to admixed controls comprising α-galactosylceramide and peptide.

The publication of Anderson et al (2014b) discloses derivatives of glycan ceramides in which the glycan moiety is substituted with a sulfide, thiol, disulfide, sulfoxide or sulfone. The derivatives are prepared via glycosylation of phytosphingosine to provide α-galactosylceramide analogue intermediates.

The publication of Anderson et al (2014a) discloses peptidylated glycan sphingolipids for use in the targeting in vivo of the CD1 protein of natural killer T-cells (NKT cells). These compounds are provided with a self-immoliative linker group between the peptidyl moiety and the amino function of the glycan sphingolipid.

The possibility to enhance further the biological activity of glycosphingolipid analogues, including ceramide conjugates, and improve their suitability for use as therapeutic agents through structural modification remains.

It is an object of the present invention to provide water dispersible ceramide conjugates and 2-branched fatty alkyl derivatives useful in the development of such therapeutic agents or the formulation of such agents. This object is to be read in the alternative with the object at least to provide a useful choice.

DISCLOSURE OF INVENTION

In a first aspect the invention provides a ceramide conjugate of the structure:

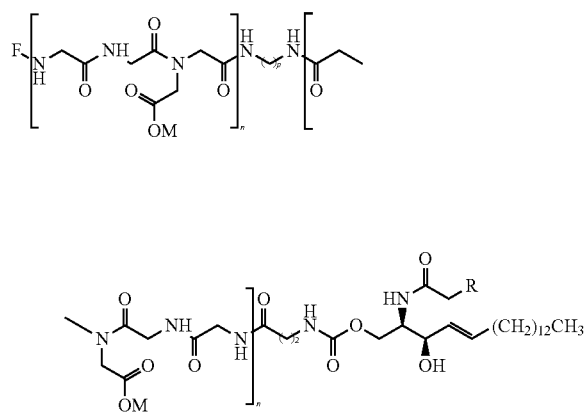

where F is H or comprises a functional moiety, M is a monovalent cation, n is the integer 1, 2, 3 or 4, p is the integer 1, 2 or 3 and R is selected from the group consisting of $C_{14-18}$ alkyl or alkenyl.

Preferably, F is selected from the group consisting of:

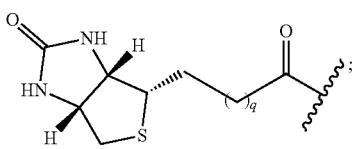

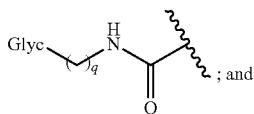

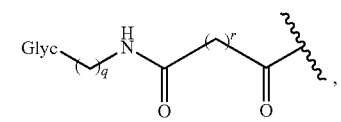

where q is the integer 2, 3 or 4, r is the integer 3, 4 or 5 and Glyc is a mono-, di-, tri- or oligosaccharide linked via a glycosidic bond.

Preferably, n and p are each the integer 2 and R is hexadecyl.

Preferably, Glyc is a mono-, di-, tri- or oligosaccharide selected from the group consisting of:

(Neu5Acα6Galβ4GlcNAcβ2Manα)$_2$3, 6Manβ4GlcNAcβ4GlcNAβ (YDS); Fucα2Galβ(H$_{di}$); Fucα2Galβ3(Fucα4)GlcNAcβ (Le$^b$); Fucα2Galβ3GlcNAcβ3Galβ4Glcβ (LNFP I); Fucα2Galβ4(Fucα3)GlcNAβ (Le$^y$); Fucα2Galβ4GlcNAcβ (H2); Galα; Galα3(Fucα2)Galβ (B$_{tri}$); Galα3(Fucα2)Galβ3(Fucα4)GlcNAβ (Ble$^b$); Galα3(Fucα2)Galβ3GalNAcα (B3); Galα3(Fucα2)Galβ3GalNAcβ (B4); Galα3(Fucα2)Galβ3GlcNAcβ (B1); Galα3(Fucα2)Galβ4(Fucα3)GlcNAcβ (Ble$^y$); Galα3(Fucα2)Galβ4GlcNAcβ (B2); Galα3Galβ4GlcNAcβ (Galili); Galα4Galβ4GlcNAcβ (P$_1$); Galα4Galβ4Glcβ (Gb3 (P$^k$)); Galα4GlcNAcβ (α-LN); GalNAcα3(Fucα2)Galβ (A$_{tri}$); GalNAcα3 (Fucα2)Galβ3(Fucα4)GlcNAcβ (ALe$^b$); GalNAcα3 (Fucα2)Galβ3GalNAcα (A3); GalNAcα3(Fucα2) Galβ3GalNAcβ (A4); GalNAcα3(Fucα2) Galβ3GlcNAcβ (A1); GalNAcα3(Fucα2)Galβ4 (Fucα3)GlcNAcβ (ALe$^y$); GalNAcα3(Fucα2) Galβ4GlcNAcβ (A2); GalNAcα3GalNAcβ (Fs2); GalNAcα3GalNAcβ3Galα4Galβ4Glcβ (Fs5); GalNAcα3Galβ (A$_{di}$); GalNAcβ; GalNAcβ3Galα4Galβ4Glcβ (P); GalNH$_2$α3(Fucα2) Galβ (AcqB); Galβ; Galβ3(Fucα4)GlcNAcβ (Le$^a$); Galβ3GalNAcα (TF); Galβ3GalNAcβ4Galβ4Glcβ (GA1); Galβ4(Fucα3)GlcNAcβ (Le$^x$); Galβ4GlcNAcβ3Galβ4GlcNAcβ (i(LN$_2$)); Galβ4GlcNAcβ3Galβ4Glcβ (LNnT); Galβ4Glcβ (Lac); GlcAβ3[GlcNAcβ4GlcAβ3]$_n$GlcNAc-aminoalditol (hyaluronate); Manα6(Manα3)Manβ (Man$_3$); Neu5Acα3Galβ4Glcβ (Neu5Ac3'LN); Neu5Acα3Galβ4Glcβ (Neu5Ac3'Lac); Neu5Acα6GalNAcαβ (SiaTn); Neu5Acα6Galβ4GlcNAcβ (Neu5Ac6'LN); and Neu5Gcα3Galβ4GlcNAcβ (Neu5Gc3'LN).

In a first embodiment of the first aspect of the invention F comprises biotin as the functional moiety and the ceramide conjugate is of the structure:

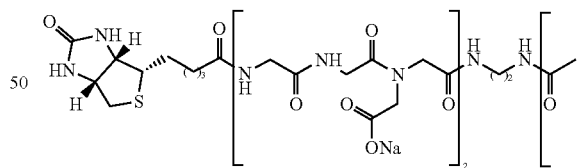

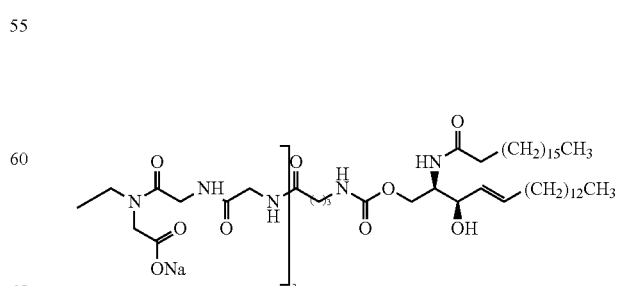

In a second embodiment of the first aspect of the invention F comprises the trisaccharide Galα3Galβ4GlcNAcβ—as the functional moiety and the ceramide conjugate is of the structure:

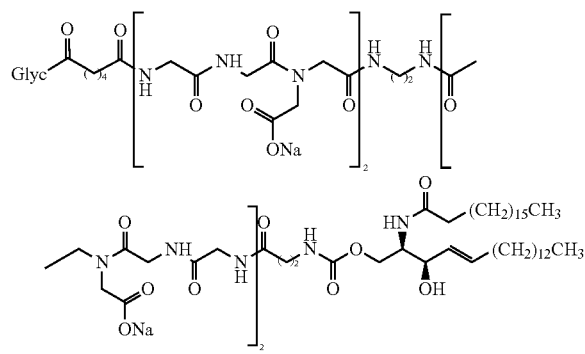

where Glyc is of the structure:

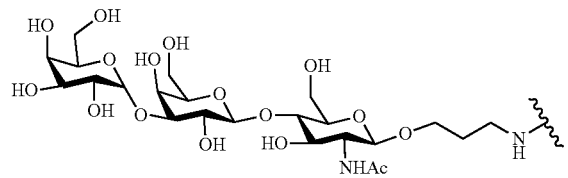

In a second aspect the invention provides a method of preparing an intermediate of the structure:

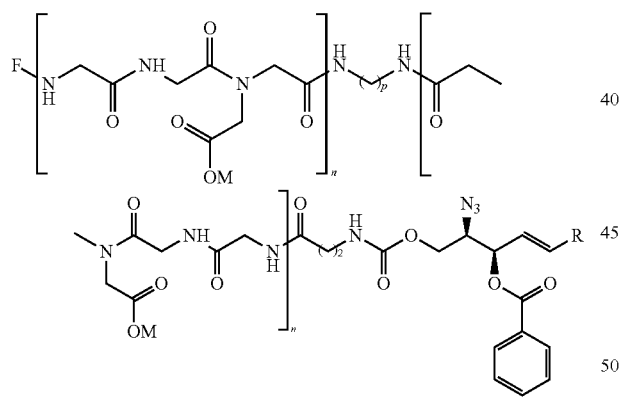

comprising the step of reacting 2-N$_3$,3-Bzl-spingosine-β-Ala-ONSu, or a homologue thereof, of the structure:

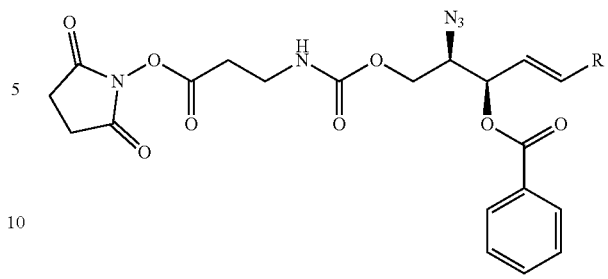

with an amine of the structure:

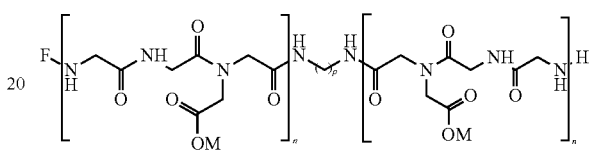

where F is a functional moiety, M is a monovalent cation, n is the integer 1, 2, 3 or 4, p is the integer 1, 2 or 3 and R is selected from the group consisting of C$_{11-15}$ alkyl or alkenyl.

In a third aspect the invention provides a method of preparing a ceramide conjugate comprising the step of N-acylation of a 1-carbamate derivative of 2-amino-4-octadecen-3-ol with an activated fatty acid.

Preferably, the fatty acid is stearic acid. Preferably, the activated fatty acid is the N-oxysuccinimide ester of the fatty acid. Preferably, the activated fatty acid is the N-oxysuccinimide ester of stearic acid.

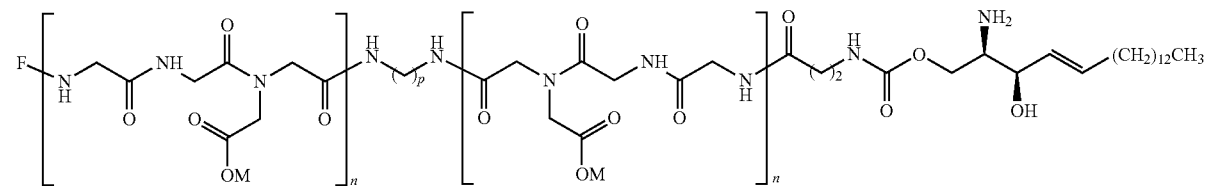

where F is H or comprises a functional moiety, M is a monovalent cation, n is the integer 1, 2, 3 or 4, p is the integer 1, 2 or 3.

Preferably, the 1-carbamate derivative of 2-amino-4-octadecen-3-ol is of the structure:

Preferably, F is selected from the group consisting of:

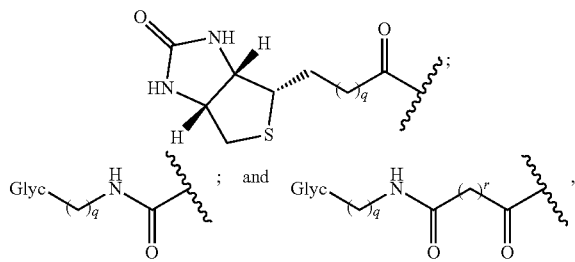

where q is the integer 2, 3 or 4, r is the integer 3, 4 or 5 and Glyc is a mono-, di-, tri- or oligosaccharide linked via a glycosidic bond.

Preferably, n and p are each the integer 2 and R is hexadecyl.

Preferably, Glyc is a mono-, di-, tri- or oligosaccharide selected from the group consisting of:

(Neu5Acα6Galβ4GlcNAcβ2Manα)$_2$3,
6Manβ4GlcNAcβ4GlcNAβ (YDS); Fucα2Galβ(H$_{di}$);
Fucα2Galβ3(Fucα4)GlcNAcβ (Le$^b$);
Fucα2Galβ3GlcNAcβ3Galβ4Glcβ (LNFP I);
Fucα2Galβ4(Fucα3)GlcNAβ (Le$^y$);
Fucα2Galβ4GlcNAcβ (H2); Galα; Galα3(Fucα2)Galβ (B$_{tri}$); Galα3(Fucα2)Galβ3(Fucα4)GlcNAβ (Ble$^b$);
Galα3(Fucα2)Galβ3GalNAcα (B3); Galα3(Fucα2)Galβ3GalNAcβ (B4); Galα3(Fucα2)Galβ3GlcNAcβ (B1); Galα3(Fucα2)Galβ4(Fucα3)GlcNAcβ (Ble$^y$); Galα3(Fucα2)Galβ4GlcNAcβ (B2); Galα3Galβ4GlcNAcβ (Galili); Galα4Galβ4GlcNAcβ (P$_1$); Galα4Galβ4Glcβ (Gb3 (P$^k$)); Galα4GlcNAcβ (α-LN); GalNAcα3(Fucα2)Galβ (A$_{tri}$); GalNAcα3(Fucα2)Galβ3(Fucα4)GlcNAcβ (ALe$^b$); GalNAcα3(Fucα2)Galβ3GalNAcα (A3); GalNAcα3(Fucα2)Galβ3GalNAcβ (A4); GalNAcα3(Fucα2)Galβ3GlcNAcβ (A1); GalNAcα3(Fucα2)Galβ4(Fucα3)GlcNAcβ (ALe$^y$); GalNAcα3(Fucα2)Galβ4GlcNAcβ (A2); GalNAcα3GalNAcβ (Fs2); GalNAcα3GalNAcβ3Galα4Galβ4Glcβ (Fs5); GalNAcα3Galβ (A$_{di}$); GalNAcβ; GalNAcβ3Galα4Galβ4Glcβ (P); GalNH$_2$α3(Fucα2)Galβ (AcqB); Galβ; Galβ3(Fucα4)GlcNAcβ (Le$^a$); Galβ3GalNAcα (TF); Galβ3GalNAcβ4Galβ4Glcβ (GA1); Galβ4(Fucα3)GlcNAcβ (Le$^x$); Galβ4GlcNAcβ3Galβ4GlcNAcβ (i(LN$_2$)); Galβ4GlcNAcβ3Galβ4Glcβ (LNnT); Galβ4Glcβ (Lac); GlcAβ3[GlcNAcβ4GlcAβ3]$_n$GlcNAc-aminoalditol (hyaluronate); Manα6(Manα3)Manβ (Man$_3$); Neu5Acα3Galβ4Glcβ (Neu5Ac3'LN); Neu5Acα3Galβ4Glcβ (Neu5Ac3'Lac); Neu5Acα6GalNAcαβ (SiaTn); Neu5Acα6Galβ4GlcNAcβ (Neu5Ac6'LN); and Neu5Gcα3Galβ4GlcNAcβ (Neu5Gc3'LN).

In a fourth aspect the invention provides a 2-branched fatty alkyl derivative of the structure:

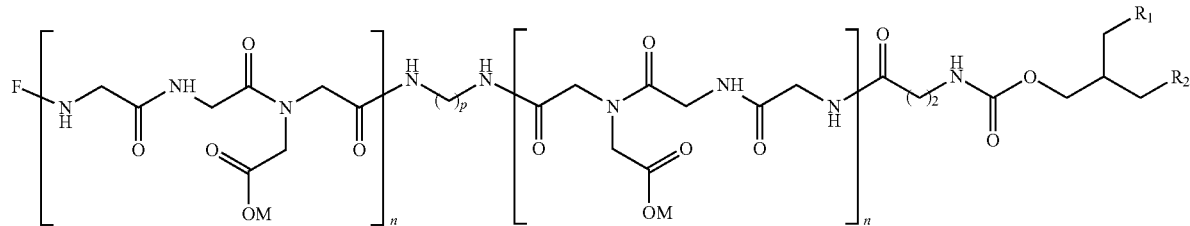

where M is a monovalent cation, n is the integer 1, 2, 3 or 4, p is the integer 1, 2 or 3 and R$_1$ and R$_2$ are independently selected from the group consisting of C$_{11-15}$ alkyl.

In a fifth aspect the invention provides a water dispersible conjugate of the structure:

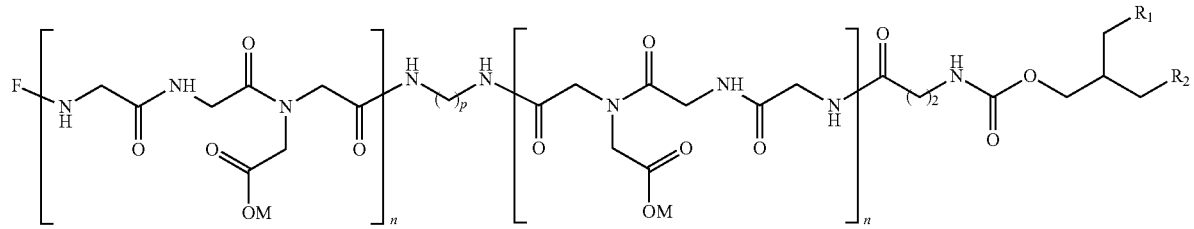

where F comprises a functional moiety, M is a monovalent cation, n is the integer 1, 2, 3 or 4, p is the integer 1, 2 or 3 and R$_1$ and R$_2$ are independently selected from the group consisting of C$_{11-15}$ alkyl.

Preferably, F is selected from the group consisting of:

where q is the integer 2, 3 or 4, r is the integer 3, 4 or 5 and Glyc is a mono-, di-, tri- or oligosaccharide linked via a glycosidic bond.

Preferably, Glyc is a mono-, di-, tri- or oligosaccharide selected from the group consisting of:

(Neu5Acα6Galβ4GlcNAcβ2Manα)$_2$3,
6Manβ4GlcNAcβ4GlcNAβ (YDS); Fucα2Galβ(H$_{di}$); Fucα2Galβ3(Fucα4)GlcNAcβ (Le$^b$); Fucα2Galβ3GlcNAcβ3Galβ4Glcβ (LNFP I); Fucα2Galβ4(Fucα3)GlcNAβ (Le$^y$); Fucα2Galβ4GlcNAcβ (H2); Galα; Galα3(Fucα2)Galβ (B$_{tri}$); Galα3(Fucα2)Galβ3(Fucα4)GlcNAβ (Ble$^b$); Galα3(Fucα2)Galβ3GalNAcα (B3); Galα3(Fucα2)Galβ3GalNAcβ (B4); Galα3(Fucα2)Galβ3GlcNAcβ (B1); Galα3(Fucα2)Galβ4(Fucα3)GlcNAcβ (Ble$^y$); Galα3(Fucα2)Galβ4GlcNAcβ (B2); Galα3Galβ4GlcNAcβ (Galili); Galα4Galβ4GlcNAcβ (P$_1$); Galα4Galβ4Glcβ (Gb3 (P$^k$)); Galα4GlcNAcβ (α-LN); GalNAcα3(Fucα2)Galβ (A$_{tri}$); GalNAcα3(Fucα2)Galβ3(Fucα4)GlcNAcβ (ALe$^b$); GalNAcα3(Fucα2)Galβ3GalNAcα (A3); GalNAcα3(Fucα2)Galβ3GalNAcβ (A4); GalNAcα3(Fucα2)Galβ3GlcNAcβ (A1); GalNAcα3(Fucα2)Galβ4(Fucα3)GlcNAcβ (ALe$^y$); GalNAcα3(Fucα2)Galβ4GlcNAcβ (A2); GalNAcα3GalNAcβ (Fs2); GalNAcα3GalNAcβ3Galα4Galβ4Glcβ (Fs5); GalNAcα3Galβ (A$_{di}$); GalNAcβ; GalNAcβ3Galα4Galβ4Glcβ (P); GalNH$_2$α3(Fucα2)Galβ (AcqB); Galβ; Galβ3(Fucα4)GlcNAcβ (Le$^a$); Galβ3GalNAcα (TF); Galβ3GalNAcβ4Galβ4Glcβ (GA1); Galβ4(Fucα3)GlcNAcβ (Le$^x$); Galβ4GlcNAcβ3Galβ4GlcNAcβ (i(LN$_2$)); Galβ4GlcNAcβ3Galβ4Glcβ (LNnT); Galβ4Glcβ (Lac); GlcAβ3[GlcNAcβ4GlcAβ3]$_n$GlcNAc-aminoalditol (hyaluronate); Manα6(Manα3)Manβ (Man$_3$); Neu5Acα3Galβ4Glcβ (Neu5Ac3'LN); Neu5Acα3Galβ4Glcβ (Neu5Ac3'Lac); Neu5Acα6GalNAcαβ (SiaTn); Neu5Acα6Galβ4GlcNAcβ (Neu5Ac6'LN); and Neu5Gcα3Galβ4GlcNAcβ (Neu5Gc3'LN).

In a first embodiment of the fifth aspect of the invention F comprises biotin as the functional moiety and the water dispersible conjugate is of the structure:

In a second embodiment of the fifth aspect of the invention F comprises the trisaccharide Galα3Galβ4GlcNAcβ— as the functional moiety and the ceramide conjugate is of the structure:

where Glyc is of the structure:

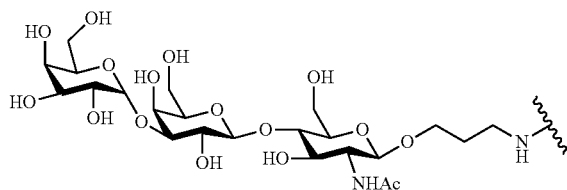

In the description and claims of this specification the following acronyms, terms and phrases have the meaning provided: "β-Ala" means 3-aminopropanoic acid; "Ad" means adipate; "alkane" means a saturated, unbranched hydrocarbon of the general formula $C_nH_{2n+2}$; "alkene" means an unsaturated alkane that contains one or more double carbon-carbon bonds; "alkenyl" means a group obtained by removing a hydrogen atom from an alkene; "alkyl" means a group obtained by removing a hydrogen atom from an alkane; "Bzl" means benzoyl; "carbamate derivative" means an organic compound of the structure $R_1NHC(O)OR_2$ where $R_1$ and $R_2$ are substituents and "1-carbamate derivative" means a carbamate derivative at the first carbon of the substituent $R_2$; "comprising" means "including", "containing" or "characterized by" and does not exclude any additional element, ingredient or step; "consisting of" means excluding any element, ingredient or step not specified except for impurities and other incidentals; "consisting essentially of" means excluding any element, ingredient or step that is a material limitation; "dispersible in water" means dispersible in pure, deionised water at 25° C. in the absence of organic solvents or surfactants to provide a dispersion at a concentration of at least 1 μmol/mL and "water dispersible" has a corresponding meaning; "DOPE" means 1,2-O-dioleoyl-sn-glycero-3-phosphatidylethanolamine; "DSC" means N,N'-disuccinimdyl carbonate; "ONSu" means N-succinimidyl ester; "$N_3$" means azide and "monovalent cation" means an ion having a single positive charge and includes the monovalent cations $H^+$, $Na^+$, $K^+$ or $(CH_3CH_2)_3N^+$. The terms "analog" and "analogue" and "homolog" and "homologue" are alternative spellings of the same words.

The terms "first", "second", "third", etc. used with reference to elements, features or integers of the subject matter defined in the Statement of Invention and Claims, or when used with reference to alternative embodiments of the invention are not intended to imply an order of preference.

Where concentrations or ratios of reagents are specified the concentration or ratio specified is the initial concentration or ratio of the reagents. Where values are expressed to one or more decimal places standard rounding applies. For example, 1.7 encompasses the range 1.650 recurring to 1.749 recurring.

In the representations of the structures or substructures of compounds the repeat of a divalent radical is represented by:

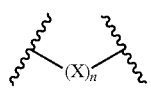

where —X— is the divalent radical repeated n times. Where the divalent radical is methylene (—$CH_2$—) the repeat of this divalent radical is represented by:

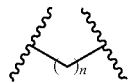

The invention will now be described with reference to embodiments or examples and the figures of the accompanying drawings pages.

DESCRIPTION OF EMBODIMENTS

Figure 1:
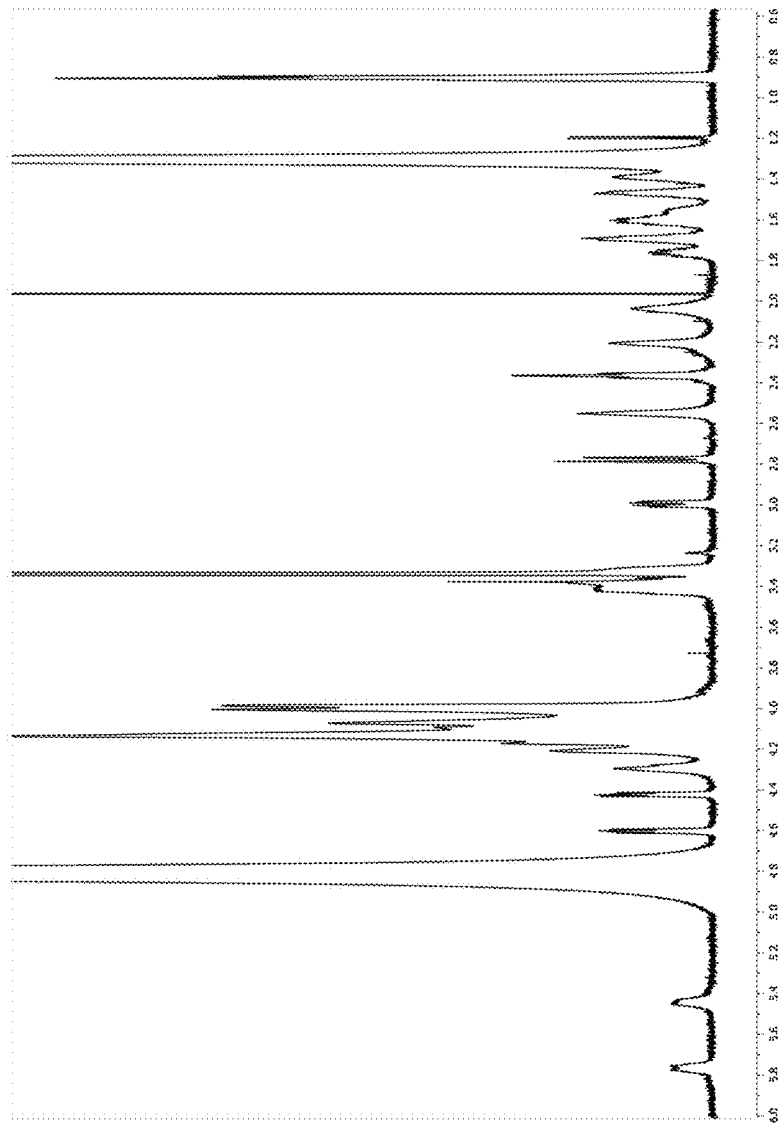
FIG. 1. $^1$H NMR spectrum of the ceramide conjugate where the functional moiety is biotin (X) (3 mg/mL in $[D_2]H_2O/[D_4]CH_3OH$ 2:1, 30° C., 700 MHz).

As stated in the publications of Anderson et al (2014a, 2014b and 2015) and Compton et al (2014), although α-galactosyl ceramide has considerable biological activity, it does have limitations such as poor solubility. The disclosures of these publications are directed to providing compounds with improved in vivo efficacy as mediated by improved targeting of the CD1 protein of NKT cells. These studies are to be distinguished from the present invention where it has been sought to provide ceramide conjugates and sphingolipid analogues that have improved solubility but are functionally equivalent to their naturally occurring counterparts with regard to their ability to incorporate and become distributed in the lipid bilayer of cell membranes. The invention resides at least in part in the use of a β-Ala derivative (IV or XIV) as an intermediate in the preparation of both the ceramide conjugates and the derivatives of sphingolipid analogues. The use of such intermediates was found to be necessary to provide a succinimidyl carbonate that would react with the amine (V or XV). For example, the intermediate (XII) was found to be reactive towards β-Ala, but not the amine (XV)

Chemistry

Ceramide Conjugates

Initial attempts to activate natural ceramide with DSC for the purposes of preparing ceramide conjugates were unsuccessful. The mixture of products obtained did not react with the amine (V). This was attributed to the formation of a cyclic carbonate of ceramide as opposed to the desired succinimidyl carbonate. It was concluded that natural ceramide was not suitable for direct conjugation via a cabamoyl linkage. The ceramide conjugates were therefore prepared via a 1-carbamate derivative of 2-amino-4-octadecen-3-ol with the ceramide moiety being formed by amidation of this intermediate. The preparation of a ceramide conjugate where the functional moiety is biotin has been prepared according to Scheme 1A-C. The amine (V) used in this scheme was prepared according to an adaptation of the method described in the publication of Bovin et al (2009). The ceramide conjugates prepared according to the described method have the advantageous property of being readily dispersible in water.

Preparation of a Ceramide Conjugate (X)

Scheme 1A

To a stirred solution of 2-N$_3$,3-Bzl-sphingosine (I) (102.7 mg, 0.239 mmol) in a mixture of dichloromethane (3 mL) and dimethylformamide (2 mL) DSC (122.5 mg, 0.478 mmol) and triethylamine (33.2 µL, 0.239 mmol) were added. The mixture was stirred for 20 hours at ambient temperature before being evaporated in vacuum (oil pump). The residue was dissolved in chloroform and extracted three times with water (3×4 mL). The chloroform extract was evaporated and the residue was thoroughly dried in vacuum. The yield of 2-N$_3$,3-Bzl-sphingosine-ONSu (II) as a white solid was 130 mg (95%). TLC: 2-N$_3$,3-Bzl-sphingosine (I) R$_f$ 0.42, 2-N$_3$,3-Bzl-sphingosine-ONSu (II) R$_f$ 0.32 (15:5:1 (v/v/v) hexane/chloroform/2-propanol).

To a stirred solution of 2-N$_3$,3-Bzl-sphingosine-ONSu (II) (130 mg, 0.227 mmol) in a mixture of dichloromethane (2 mL) and dimethylformamide (2 mL) a solution of β-Ala (40.5 mg, 0.405 mmol: 405 µL of solution 100 mg/mL β-Ala and 86 µL/mL trifluoroacetic acid in DMSO) and triethylamine (253 µL, 1.816 mmol) were added. The mixture was stirred for 19 hours at ambient temperature before evaporating in vacuum (oil pump) and drying. The residue was extracted in a mixture of chloroform (4 mL), water (4 mL) and 2M hydrochloric acid (0.12 mL). The chloroform layer was washed twice with water (2×4 mL), evaporated and the residue was dried in vacuum. The crude material was purified on a silica gel column (volume circa 80 ml) in 15:5:1 (v/v/v) hexane/chloroform/2-propanol eluted with 15:5:1 (v/v/v) hexane/chloroform/2-propanol including 0.5% (v/v) acetic acid. Collected fractions were evaporated and the residue dissolved in chloroform. The solution of the residue was washed twice with water (2×3 mL), diluted with acetonitrile (3 mL) and evaporated. Thorough drying of the residue yielded 105.5 mg (85%) of pure 2-N$_3$,3-Bzl-sphingosine-β-Ala (III) as a colorless syrupy glass. TLC: R$_f$ 0.12 (15:5:1 (v/v/v) hexane/chloroform/2-propanol); R$_f$ 0.49 (4:1 (v/v) chloroform/2-propanol).

$^1$H NMR of 2-N$_3$,3-Bzl-sphingosine-β-Ala (III) (700 MHz, [D]CHCl$_3$/[D$_4$]CH$_3$OH 1:1, 30° C.): δ 8.210 (m, 2H; orto-H of Bzl), 7.766 (m, 1H; para-H of Bzl), 7.636 (m, 2H; meta-H of Bzl), 6.114 (m, 1H; =CH), 5.754 (m, 2H; CH= and =C—CH—O), 4.383 (dd, J=11.4, 4.6 Hz, 1H; OCH), 4.274 (dd, J=11.4, 7.7 Hz, 1H; OCH'), 4.172 (m, 1H; CH—N$_3$), 3.565 (t, J=6.6 Hz, 2H; NCH$_2$ of β-Ala), 2.693 (t, J=6.6 Hz, 2H; CH$_2$CO of β-Ala), 2.260 (q, J=7.1, 7.1, 6.8 Hz, 2H; =C—CH$_2$), 1.565 (m, 2H; =C—C—CH$_2$), 1.440 (m, 20H; 10 CH$_2$), 1.043, (t, J=7.1 Hz, 3H; CH$_3$) ppm.

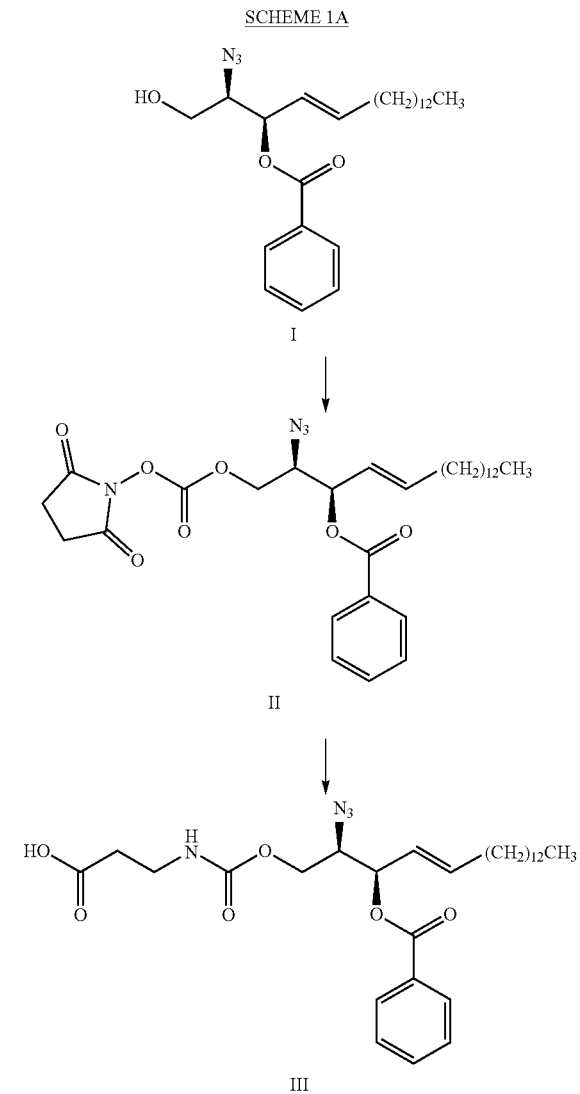

SCHEME 1A

Scheme 1B

To a stirred solution of 2-N$_3$,3-Bzl-sphingosine-β-Ala (III)(40 mg, 73.4 µmol) in 1,2-dichloroethane (1 mL) a solution of DSC (37.6 mg, 147 µmol: 470 µL of 80 mg/mL solution in dimethylformamide) and triethylamine (15.3 µL, 110 µmol) were added, and the mixture was stirred for 1.5 hours at ambient temperature. The reaction mixture was acidified with acetic acid (100 µL) and placed on a Sephadex LH-20 column (volume 90 mL) and eluted with 2:1 (v/v) chloroform/2-propanol including 0.5% (v/v) acetic acid. Fractions containing 2-N$_3$,3-Bzl-Sphingosine-β-Ala-ONSu (IV) were combined, evaporated and the residue dried in vacuum. The yield of 2-N$_3$,3-Bzl-sphingosine-β-Ala-ONSu (IV) as a white solid was 42.4 mg (90%). TLC: R$_f$ 0.56 (15:5:1 (v/v/v) hexane/chloroform/2-propanol).

To a stirred suspension of the biot-CMG(2) amine (V) (44 mg, 34.7 µmol) in dimethyl sulfoxide (2 mL) a solution of 2-N$_3$,3-Bzl-sphingosine-β-Ala-ONSu (IV) (24.5 mg, 38.1 micromole) in 1,2-dichloroethane (0.49 mL), water (0.7 mL) and 1M aqueous sodium bicarbonate (34.7 µL) were added. The mixture was stirred for 2 hours at ambient temperature before acidifying the reaction mixture with acetic acid (6 µL) and placing on a Sephadex LH-20 column (volume 130 mL) and eluting with 40:14:10:1 (v/v/v/v) water/methanol/2-propanol/chloroform. Fractions containing 2-$N_3$,3-Bzl-sphingosine-β-Ala-CMG(2)-biot (VI) were combined, evaporated, the residue dissolved in water (3 mL) and then freeze-dried. The yield of 2-$N_3$,3-Bzl-sphingosine-β-Ala-CMG(2)-biot (VI) as a white solid was 56.7 mg (90% based on biot-CMG(2) amine (V)). TLC: $R_f$ 0.64 (1:3:1 (v/v/v) dichloromethane/ethanol/water); $R_f$ 0.40 (1:3:1 (v/v/v) dichoromethane/ethanol/water including 2% (v/v) acetic acid volume).

$^1$H NMR of 2-$N_3$,3-Bzl-sphingosine-β-Ala-CMG(2)-biot (VI) (700 MHz, [$D_2$]$H_2$O/[$D_4$]$CH_3$OH 1:1, 30° C.): δ8.035 (m, 2H; orto-H of Bzl), 7.653 (m, 1H; para-H of Bzl), 7.507 (m, 2H; meta-H of Bzl), 5.951 (m, 1H; =CH), 5.602 (m, 2H; CH= and =C—CH—O), 4.581 (dd, J=7.9, 5.0 Hz, 1H; NHC$\underline{H}$ of biotin), 4.396 (dd, J=7.9, 4.5 Hz, 1H; NHC$\underline{H}$ of biotin), 4.333-3.899 (total 35H; 4 $CH_2$COO, 12 NC$\underline{H_2}$CO, $CH_2$O, CH—$N_3$), 3.469-3.351 (m, 6H; NC$\underline{H_2}$$CH_2$N and $CH_2$N of β-Ala), 3.289 (m, 1H; NHCHC$\underline{H}$ of biotin), 2.985 (dd, J=12.9, 4.8 Hz, 1H; NHCHC$\underline{H}$ of biotin), 2.761 (d, J=12.9 Hz, 1H; NHCHC$\underline{H}$ of biotin), 2.554 (broad t, 2H; $CH_2$CO of β-Ala), 2.354 (m, 2H; COC$H_2$ of biotin), 2.086 (broad, 2H; =C—$CH_2$), 1.756 (m, 1H; COC$H_2$$CH_2$$CH_2$C$\underline{H}$ of biotin), 1.677 (m, 2H; COC$H_2$C$\underline{H_2}$$CH_2$$CH_2$ of biotin), 1.593 (m, 1H; COC$H_2$$CH_2$$CH_2$C$\underline{H}$ of biotin), 1.462 (m, 2H; COC$H_2$$CH_2$C$\underline{H_2}$$CH_2$ of biotin), 1.353 (m, 2H; =C—C—$CH_2$), 1.224 (m, 20H; 10 $CH_2$), 0.865 (t, J=7.0 Hz, 3H; $CH_3$) ppm.

MALDI TOF mass-spectrum of 2-$N_3$,3-Bzl-sphingosine-β-Ala-CMG(2)-biot (VI) ($C_{73}H_{108}N_{20}O_{27}$S, MW isotopic=1729). M/z 1704: M(-$N_2$+2H)+H; 1726: M(-$N_2$+2H)+Na; 1730: M+H; 1752; MNa+H; 1768: MK+H; 1774: M$Na_2$+H; 1790: MNaK+H. Instrument: FLEX-PC, DHB matrix.

To a stirred solution 2-$N_3$,3-Bzl-sphingosine-β-Ala-CMG(2)-biot (VI) (49.1 mg, 27.01 µmol) in water (4.91 mL), methanol (9.82 mL) and triethylamine (0.737 mL) were added. The mixture was kept for 77 hours at ambient temperature before evaporating the reaction mixture and thoroughly drying the residue in vacuum and freeze drying. The 2-$N_3$-sphingosine-β-Ala-CMG(2)-biot (VII) was used without purification. TLC: $R_f$ 0.34 (1:3:1 (v/v/v) dichloromethane/ethanol/water including 2% (v/v) acetic acid).

$^1$H NMR of 2-$N_3$-sphingosine-β-Ala-CMG(2)-biot (VII) (700 MHz, [$D_2$]$H_2$O/[$D_4$]$CH_3$OH 1:1, 30° C.): δ 5.812 (m, 1H; CH=), 5.518 (m, 1H; =CH), 4.593 (dd, J=7.9, 5.0 Hz, 1H; NHC$\underline{H}$ of biotin), 4.409 (dd, J=7.9, 4.5 Hz, 1H; NHC$\underline{H}$ of biotin), 4.272-3.934 (total 35H; 4 $CH_2$COO, $\overline{12}$ NC$\underline{H_2}$CO, $CH_2$O, CH—$N_3$), 3.720 (m, 1H; =C—CH—O), 3.459-3.352 (m, 6H; NC$\underline{H_2}$$CH_2$N and $CH_2$N of β-Ala), 3.304 (m, 1H; NHCHC$\underline{H}$ of biotin), 2.998 (dd, J=12.9, 4.9 Hz, 1H; NHCHC$\underline{H}$ of biotin), 2.769 (d, J=12.9 Hz, 1H; NHCHC$\underline{H}$ of biotin), 2.557 (t, J=6.5 Hz, 2H; $CH_2$CO of β-Ala), 2.360 (m, 2H; COC$H_2$ of biotin), 2.095 (m, 2H; =C—$CH_2$), 1.771 (m, 1H; COC$H_2$$CH_2$$CH_2$C$\underline{H}$ of biotin), 1.696 (m, 2H; COC$H_2$C$\underline{H_2}$$CH_2$$CH_2$ of biotin), 1.610 (m, 1H; COC$H_2$$CH_2$$CH_2$C$\underline{H}$ of biotin), 1.469 (m, 2H; COC$H_2$$CH_2$C$\underline{H_2}$$CH_2$ of biotin), 1.418 (m, 2H; =C—C—$CH_2$), 1.281 (m, 20H; 10 $CH_2$), 0.898 (t, J=7.1 Hz, 3H; $CH_3$) ppm.

Scheme 1C

To a stirred solution of the unpurified 2-$N_3$-sphingosine-β-Ala-CMG(2)-biot (VII) (27.01 µmol) in water (1.5 mL), methanol (4.5 mL), dithiothreitol (150 mg) and triethylamine (30 µL) were added. The mixture was stirred for 48 hours at ambient temperature and the reaction mixture evaporated to dryness. The residue vas dissolved in 2 ml of 2:1 (v/v) water/2-propanol, placed on a Sephadex LH-20 column (volume 90 mL) and eluted with 2:1 (v/v) water/2-propanol including 0.05 M Py·HOAc. Fractions containing sphingosine-β-Ala-CMG(2)-biot (VIII) were combined, evaporated and the residue dried in vacuum. The yield of sphingosine-β-Ala-CMG(2)-biot (VIII) as a white solid was 44.3 mg (89% based on 2-$N_3$,3-Bzl-Sphingosine-β-Ala-CMG(2)-biot (VII) if calculated as tripyridunium salt). TLC: $R_f$ 0.29 (1:3:1 (v/v/v) dichloromethane/ethanol/water including 2% (v/v) acetic acid), ninhydrin-positive.

To a stirred solution of sphingosine-β-Ala-CMG(2)-biot (VIII) (44.3 mg, 24.1 µmol) in a mixture of water (2 mL) and 2-propanol (3 mL) 1 M aqueous sodium bicarbonate (160 µL) and a solution of N-oxysuccinimide ester of stearic acid (20.3 mg, 53 micromole) in 1,2-dichloroethane (0.27 mL) were added, and the mixture stirred for 8 hours at ambient temperature. Additional portions of N-oxysuccinimide ester of stearic acid (20.3 mg, 53 µmol) in 1,2-dichloroethane (0.27 mL) and 1 M aqueous sodium bicarbonate (160 µL) were added and the mixture was stirred for 15 hours at ambient temperature. The reaction mixture was acidified with acetic acid (18 µL), evaporated and the residue dried in vacuum. The reaction products were separated on a silica gel column (volume 75 mL) prepared in 4:1 (v/v) chloroform/methanol and eluted with 2:6:1 (v/v/v) chloroform/methanol/water. Chromatography was accompanied by

SCHEME 1B

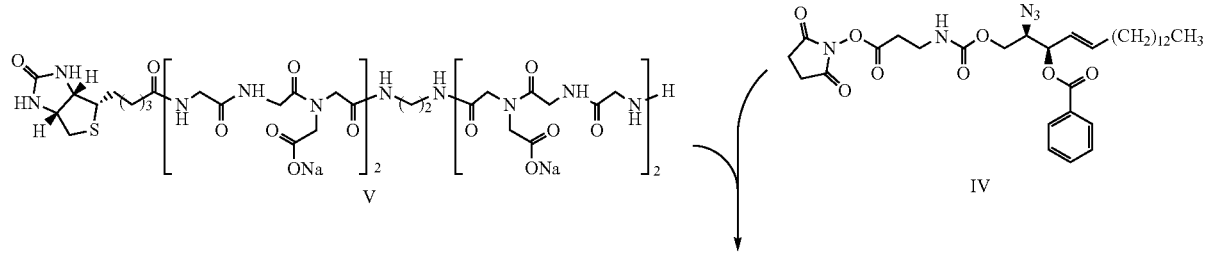

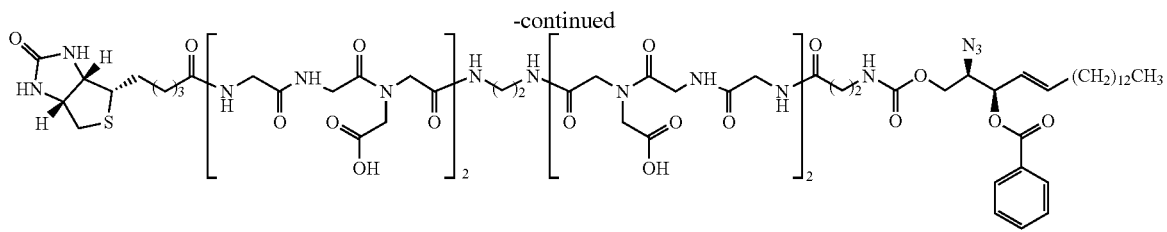

VI

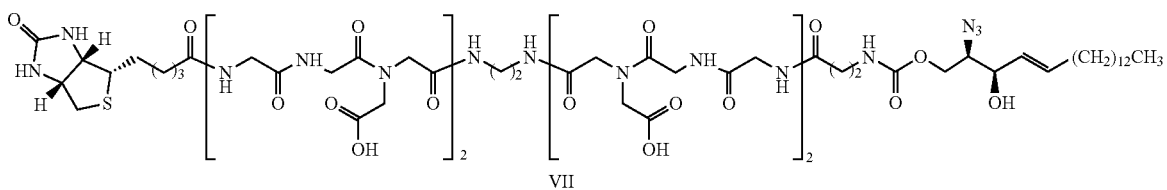

VII self-oxidation of the biotin group into biotin(S-oxide). Repeated (twice) separation of ceramide-β-Ala-CMG(2)-biot (X), ceramide-β-Ala-CMG(2)-biot(S-oxide) (IX) and minor sphingosine-β-Ala-CMG(2)-biot(S-oxide) (oxidation of unreacted sphingosine-β-Ala-CMG(2)-biot (VIII)) on a silica gel column (volume 75 mL) prepared in 4:1 (v/v) chloroform/methanol and eluted with 1:2:1 (v/v/v) dichloromethane/ethanol/water including 1% Py provided 20.5 mg (yield 45%) of pure freeze-dried ceramide-β-Ala-CMG(2)-biot(S-oxide) (IX). TLC: ceramide-β-Ala-CMG(2)-biot (X) $R_f$ 0.62; ceramide-β-Ala-CMG(2)-biot(S-oxide) (IX) $R_f$ 0.54; sphingosine-β-Ala-CMG(2)-biot(S-oxide) $R_f$ 0.46 (1:3:1 (v/v/v) dichloromethane/ethanol/water including 1% (v/v) Py).

$^1$H NMR of ceramide-β-Ala-CMG(2)-biot(S-oxide) (IX) (700 MHz, [D$_2$]H$_2$O/[D$_4$]CH$_3$OH 2:1, 30° C.): δ 5.769 (m, 1H; CH=), 5.454 (m, 1H; =CH), under water (NHCH of biotin-S-oxide), 4.721 (dd, J=8.9, 5.5 Hz, 1H; NHCH of biotin-S-oxide), 4.331-3.897 (total 36H; 4 CH$_2$COO, 12 NCH$_2$CO, CH$_2$O, CHN, =C—CH—O), 3.639 (d, J=13.5, 1,9 Hz, 1H; NHCHCH of biotin-S-oxide), 3.446-3.344 (m, 7H; NCH$_2$CH$_2$N, CH$_2$N of β-Ala and NHCHCH of biotin-S-oxide), 3.219 (dd, J=13.5, 6.7 Hz, 1H; NHCHCH of biotin-S-oxide), 2.536 (broad t, 2H; CH$_2$CO of β-Ala), 2.394 (t, J=7.3 Hz, 2H; COCH$_2$ of biotin-S-oxide), 2.208 (broad t, 2H; COCH$_2$ of stearoyl), 2.030 (m, 2H; =C—CH$_2$), 1.901 (m, 2H; COCH$_2$CH$_2$ of stearoyl), 1.734 and 1.593 (m, 6H; 3CH$_2$ of biotin-S-oxide), 1.304 (broad s, 50H; 25CH$_2$), 0.902 (t, J=6.9 Hz, 3H; CH$_3$), 0.894 (broad t, J=7.1 Hz, 3H; CH$_3$) ppm.

MALDI TOF mass-spectrum of ceramide-β-Ala-CMG (2)-biot(S-oxide) (IX) (C$_{84}$H$_{140}$N$_{18}$O$_{28}$S, MW=1881). M/z 1882: M+H; 1904: MNa+H; 1920: MK+H; 1926: MNa$_2$+H; 1942: MNaK+H; 1948: MNa$_3$+H; 1964: MKNa$_2$+H; 1970: MNa$_4$+H; 1986: MKNa$_3$+H; 1992: MNa$_4$+Na; 2008: MNa$_4$+K. Instrument: FLEX-PC, DHB matrix.

To a stirred solution of ceramide-β-Ala-CMG(2)-biot(S-oxide)(IX)(20.5 mg, 10.89 μmol) in a water (1.314 mL) N-methyl-mercaptoacetamide (373 μL) was added and the mixture kept for 69 hours at 40° C. The reaction mixture was placed on a Sephadex LH-20 column (volume 90 mL) and eluted with 2:1 (v/v) water/2-propanol including 0.03 M acetic acid and 0.06 M Py). Fractions containing pure ceramide-β-Ala-CMG(2)-biot (X) were combined, evaporated and the residue thoroughly dried in vacuum. The residue was dissolved in water (1 mL), titrated to pH 6.5 with 0.1 M sodium bicarbonate and freeze-dried. The yield of ceramide-β-Ala-CMG(2)-biot (X) as a white solid was 15.8 mg (74%). TLC: $R_f$ 0.64 (1:3:1 (v/v/v) dichloromethane/ethanol/water).

$^1$H NMR of ceramide-β-Ala-CMG(2)-biot (X) (700 MHz, [D$_2$]H$_2$O/[D$_4$]CH$_3$OH 2:1, 30° C.): δ 5.764 (m, 1H; CH=), 5.443 (m, 1H; =CH), 4.603 (dd, J=7.9, 4.9 Hz, 1H;

SCHEME 1C

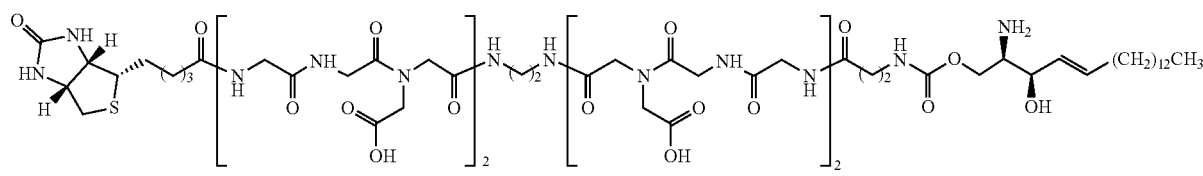

VIII

-continued

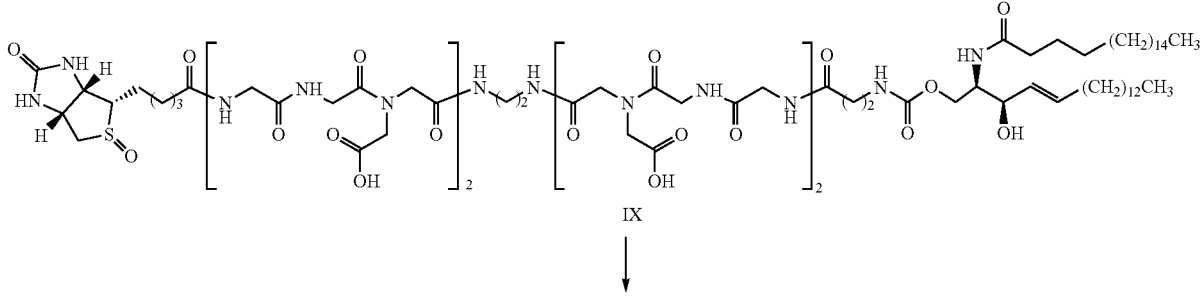

IX

↓

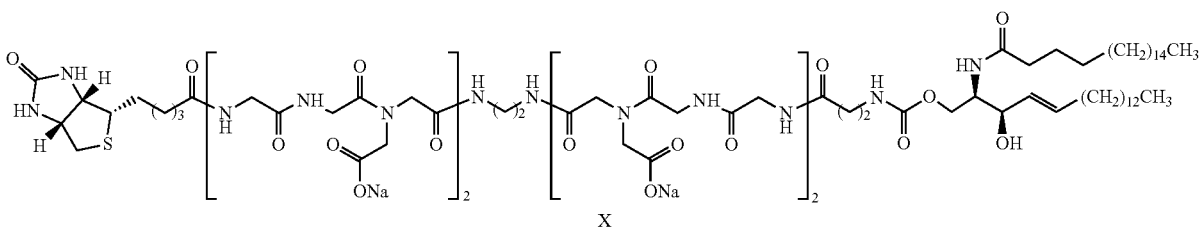

X

NHC<u>H</u> of biotin), 4.423 (dd, J=7.9, 4.6 Hz, 1H; NHC<u>H</u> of biotin), 4.312-3.964 (total 36H; 4 CH$_2$COO, 12 NCH$_2$CO, CH$_2$O, CHN and =C—CH—O), 3.444-3.352 (m, 6H; NCH$_2$CH$_2$N and CH$_2$N of β-Ala), 3.313 (m, 1H; NHCHC<u>H</u> of biotin), 2.997 (dd, J=12.9, 4.8 Hz, 1H; NHCHC<u>H</u> of biotin), 2.778 (d, J=12.9 Hz, 1H; NHCHC<u>H</u> of biotin), 2.552 (t, J=6.5 Hz, 2H; CH$_2$CO of β-Ala), 2.365 (m, 2H; COCH$_2$ of biotin), 2.206 (broad t, 2H; COCH$_2$ of stearoyl), 2.039 (m, 2H; =C—CH$_2$), 1.759, 1.691, 1.601, 1.558 and 1.469 (m, total 8H; 6H of biot and COCH$_2$C<u>H</u>$_2$ of stearoyl), 1.390 (m, 2H; =C—C—CH$_2$), 1.299 (m, 48H; 24 CH$_2$), 0.905 (t, J=6.6 Hz, 3H; CH$_3$), 0.895 (broad t, J=7.0 Hz, 3H; CH$_3$) ppm.

MALDI TOF mass-spectrum of ceramide-β-Ala-CMG(2)-biot (X) (C$_{84}$H$_{140}$N$_{18}$O$_{28}$S, MW=1865). M/z 1866: M+H; 1888: M+Na; 1904: M+K; 1910: MNa+Na; 1926: MNa+K; 1932: MNa$_2$+Na; 1948: MNa$_2$+K; 1954: MNa$_3$+Na; 1970: MNa$_3$+K; 1976: MNa$_4$+Na. Instrument: FLEX-PC, DHB matrix.

Derivatives of Sphingolipid Analogues

Sphingolipid analogues comprising a 2-(alkyl)alkyl membrane anchor, e.g. 2-(teradecyl)hexadecyl, are mimetics of the ceramide conjugates that retain the advantageous property of being dispersible in water. In preferred embodiments of these structural mimetics, the fully saturated dialkyl alcohol 2-(tetradecyl)hexadecanol is substituted for the acylated sphingosine of ceramide. A sphingolipid analogue where the functional moiety is biotin has been prepared according to Scheme 2.

The amine (XV) is prepared according to the method described in the publication of Bovin et al (2009). The preparation of the β-Ala derivative (XIV) was found to be necessary to provide a succinimidyl carbonate that would react with the amine (XV). The intermediate (XII) was found to be reactive towards β-Ala, but not the amine (XV).

The preparation of glycosphingolipid analogues according to Scheme 3 is also anticipated. In both schemes it will be recognised that a range of sphingolipid analogues may be prepared using homologues of 2-(tetradecyl)hexadecanol. Homologues comprising alkyl chains of a length comparable with that of ceramide are preferred.

SCHEME 2

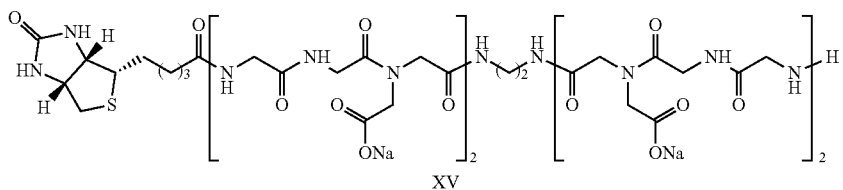

XV

-continued

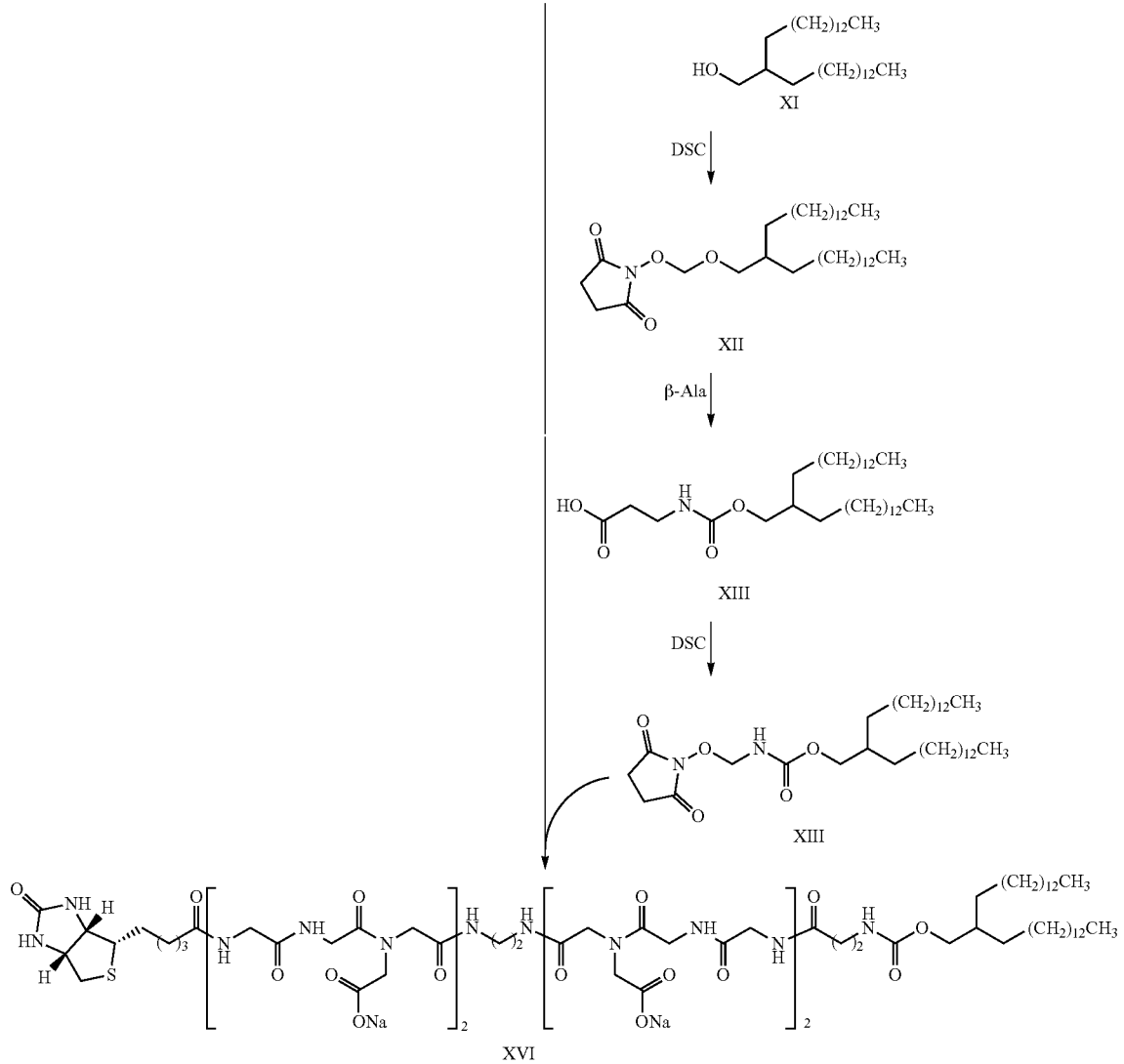

Preparation of a Sphingolipid Analogue (XVI)

To a stirred solution of 2-(tetradecyl)hexadecanol (XI) (Katayama Chemical Industries Co., Limited) (15.3 mg, 34.87 µmol) in a mixture of dichloromethane (1 mL) and dimethylformamide (0.6 mL) a solution of DSC (71.5 mg, 279 µmol) in dimethylformamide (0.893 mL) and triethylamine (19.4 µL, 139 µmol) were added. The mixture was stirred for 24 hours at ambient temperature and then the reaction mixture acidified with acetic acid (96 µL) before being placed on a Sephadex LH-20 column (volume 90 mL) and eluted with 2:1 (v/v) trichloromethane/2-propanol plus 0.5% (v/v) acetic acid. Fractions containing the intermediate (XII) were combined, evaporated and the residue dried in vacuum. The yield of the intermediate (XII) as a white solid was 19.1 mg (94%). TLC: $R_f$ 0.35 (15:5:1 (v/v/v) hexane/trichloromethane/2-propanol).

To a stirred solution of the intermediate (XII) (19.1 mg, 32.94 µmol) in a mixture of 1,2-dichloroethane (1 mL) and dimethylformamide (2 mL) a volume of 106 µL of a 100 mg/mL solution of β-Ala (10.6 mg, 119 µmol) with 86 µL/mL trifluoroacetic acid in DMSO and triethylamine (66 µL, 475 µmol) were added. The mixture was stirred for 17 hours at ambient temperature before being acidified with acetic acid (60 µL) and evaporated with 5 mL of 2-propanol to a minimum volume. The sample was placed on a Sephadex LH-20 column (volume 90 mL) and eluted with 2:1 (v/v) trichloromethane/2-propanol plus 0.5 M Py·AcOH. Fractions containing the intermediate (XIII) were combined, evaporated and the residue dried in vacuum. The yield of the intermediate (XIII) as a white solid was 17.4 mg (95%). TLC: $R_f$ 0.38 (2:4:1 (v/v/v) hexane/trichloromethane/2-propanol). $^1$H NMR of intermediate (XIII) (700 MHz, [D]CHCl$_3$/[D$_4$]CH$_3$OH 1:1, 30° C.): δ 4.098 (d, J=5.4 Hz, 2H; CH$_2$O), 3.549 (t, J=6.5 Hz, 2H; CH$_2$N of β-Ala), 2.684 (t, J=6.5 Hz, 2H; CH$_2$CO of β-Ala), 1.766 (m, 1H; OCH$_2$C$\underline{H}$), 1.433 (m, 52H; 26 CH$_2$), 1.046, (t, J=7.1 Hz, 6H; 2 CH$_3$) ppm.

To a stirred solution of the intermediate (XIII) (11.3 mg, 20.4 µmol) in a mixture of 1,2-dichloroethane (1 mL) and dimethylformamide (0.35 mL) a 131 µL volume of a 80 mg/mL solution of DSC (10.5 mg, 41 µmol) in dimethylformamide and triethylamine (4.3 µL, 31 µmol) were added. The mixture was stirred for 2 hours at ambient temperature and the reaction mixture acidified with acetic acid (100 µL).

The acidified mixture was placed on Sephadex LH-20 column (volume 90 mL) and eluted with 2:1 (v/v) trichloromethane/2-propanol plus 0.5% (v/v) acetic acid. Fractions containing the activated intermediate (XIV) were combined, evaporated and the residue dried in vacuum. The yield of the activated intermediate (XIV) as a white solid was 12.7 mg (96%). TLC: $R_f$=0.72 (2:4:1 (v/v/v) hexane/trichloromethane/2-propanol).

Figure 2:
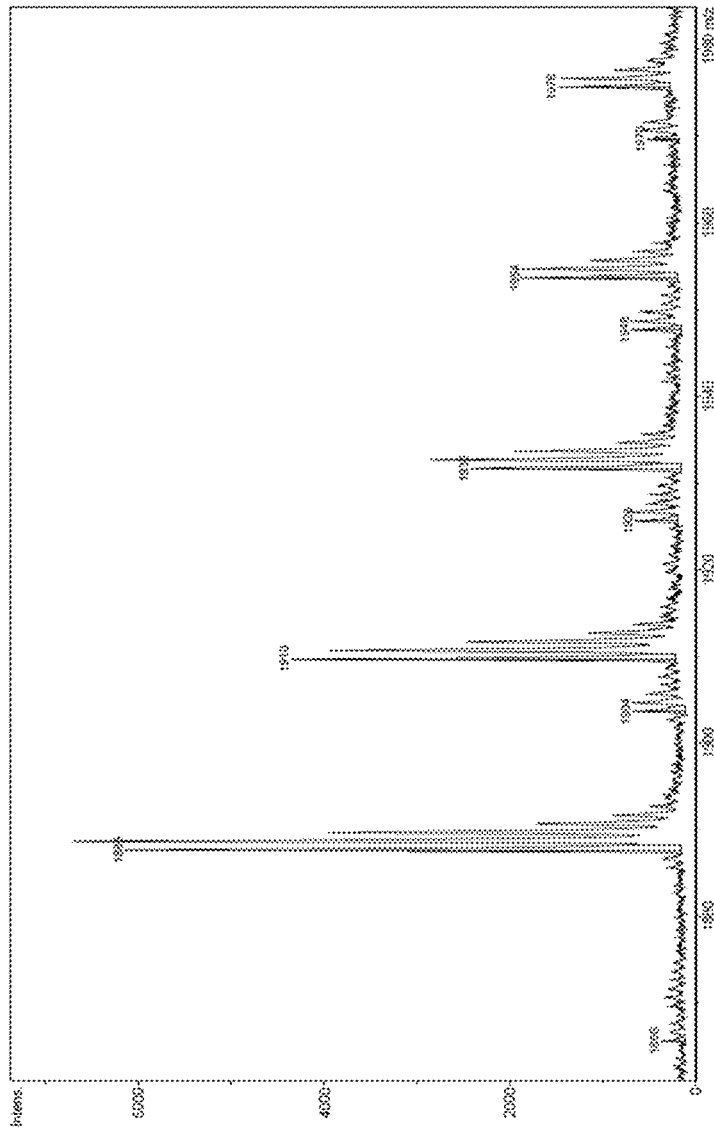
FIG. 2. MALDI TOF mass-spectrum of the ceramide conjugate where the functional moiety is biotin (X) ($C_{84}H_{140}N_{18}O_{27}S$, MW isotopic 1865). 1866: M+H; 1888: M+Na; 1904: M+K; 1910: MNa+Na; 1926: MNa+K; 1932: MNa2+Na; 1948: MNa2+K; 1954: MNa3+Na; 1970: MNa3+K; 1976: MNa4+Na. Instrument: FLEX-PC, DHB matrix.

To a stirred suspension of the amine (XV) (22.3 mg, 17.56 μmol) in dimethyl sulfoxide (1.5 mL) a solution of the activated intermediate (XIV) (12.7 mg, 19.51 μmol) in 1,2-dichloroethane (0.25 mL), water (0.35 mL) and 1 M aqueous sodium bicarbonate (35.2 μL) were added, and the mixture stirred for 5 hours at ambient temperature. The reaction mixture was acidified with acetic acid (3 μL), evaporated with 3 mL of 1:1 (v/v) 2-propanol/water to a minimum volume and placed on a Sephadex LH-20 column (volume 90 mL). The column was eluted with 1:2 (v/v) 2-propanol/water plus 3% (v/v) dichloromethane and 0.3% (v/v) Py by volume). Fractions containing the sphingolipid analogue (XVI) were combined, evaporated and the residue thoroughly dried in vacuum. The residue was dissolved in water (1 mL), titrated to pH 6.5 with 0.1 M sodium bicarbonate and freeze-dried. The yield of the sphingolipid analogue (XVI) as a white solid was 29.2 mg (91% based on the amine (XV)). TLC: $R_f$ 0.61 (2:6:1 (v/v/v) trichloromethane/methanol/water). $^1$H NMR of the sphingolipid analogue (XVI) (see FIG. 1) (700 MHz, 1:1 (v/v) [D$_2$]H$_2$O/[D$_4$]CH$_3$OH, 30° C.): δ 4.590 (dd, J=7.9, 4.7 Hz, 1H; NHC$\underline{H}$ of biotin), 4.408 (dd, J=7.9, 4.6 Hz, 1H; NHC$\underline{H}$ of biotin), 4.293-3.917 (total 34H; 4 CH$_2$COO, 12 NCH$_2$CO, CH$_2$O), 3.428-3.343 (m, 6H; NCH$_2$CH$_2$N and CH$_2$N of β-Ala), 3.302 (m, 1H; NHCHC$\underline{H}$ of biotin), 2.993 (dd, J=12.9, 5.0 Hz, 1H; NHCHC$\underline{H}$ of biotin), 2.767 (d, J=12.9 Hz, 1H; NHCHC$\underline{H}$ of biotin), 2.546 (t, J=6.5 Hz, 2H; CH$_2$CO of β-Ala), 2.359 (m, 2H; COCH$_2$ of biotin), 1.768, (m, 1H; COCH$_2$CH$_2$CH$_2$CH of biotin), 1.695 (m, 2H; COCH$_2$CH$_2$CH$_2$C$\overline{\underline{H}}_2$ of biotin), 1.609 (m, 2H; COCH$_2$C$\overline{\underline{H}}_2$CH$_2$CH of biotin and OCH$_2$C$\underline{H}$), 1.468 (m, 2H; COCH$_2$CH$_2$CH$_2$C$\overline{\underline{H}}_2$ of biotin), 1.312 (m, 52H; 26 CH$_2$), 0.919, (t, J=7.0 Hz, 6H; 2 CH$_3$) ppm. MALDI TOF mass-spectrum of the sphingolipid analogue (XVI) (see FIG. 2) (C$_{78}$H$_{131}$N$_{17}$O$_{25}$S, MW=1739). M/z 1740: M+H; 1762; MNa+H; 1778: MK+H; 1784: MNa$_2$+H; 1800: MNaK+H; 1806: MNa$_3$+H; 1822: MKNa$_2$+H. Instrument: FLEX-PC, DHB matrix.

Avidinylated functional moieties may be conjugated to the ceramide conjugate (X) or the sphingolipid analogue (XVI) under biocompatible conditions exploiting non-covalent avidin-biotin binding. Alternatively, it is anticipated that ceramide conjugates and sphingolipid analogues may be prepared by covalent attachment of the functional moiety. For example, it is anticipated that glycosphingolipid analogues may be prepared according to Scheme 3. In accordance with this scheme equimolar amounts of the activated β-Ala derivative (XIV) and the diamine (XVII) are reacted to provide the membrane anchor (XVIII). The membrane anchor (XVIII) is then reacted with an activated saccharide, such as the N-succimidyl carbamate of a 3-aminopropylglycoside (XIX).

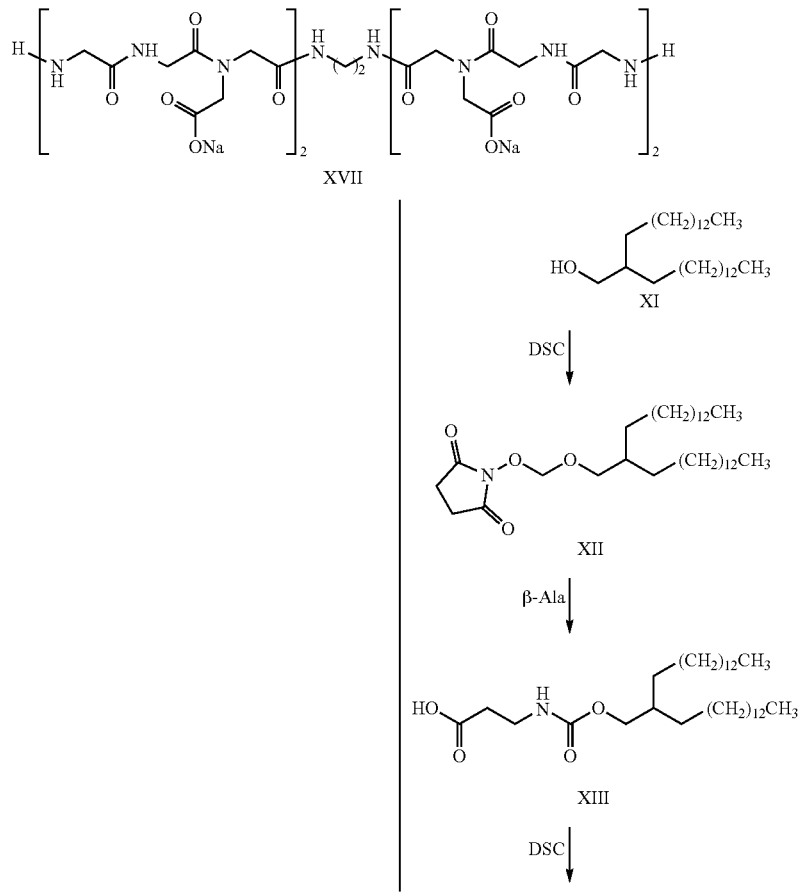

SCHEME 3

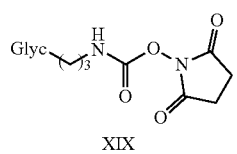

XIX

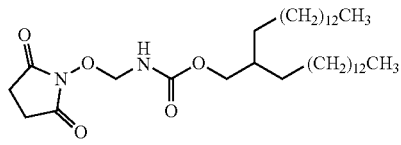

XIV

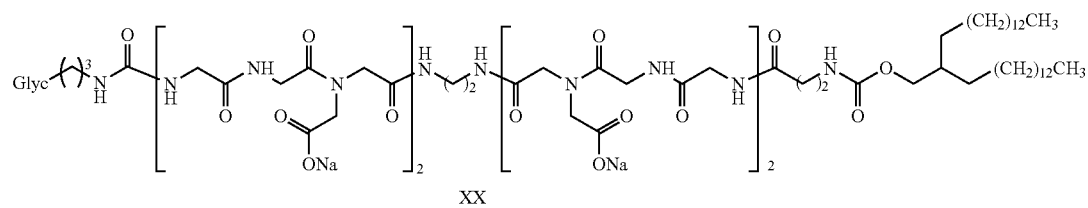

XVIII

XX

A non-limiting example of a 3-aminopropylglycoside (XIX) is 3-aminopropyl-α-D-galactopyranosyl-(1→3)-β-D-galactopyranosyl-(1→4)-2-acetamido-2-deoxy-β-D-glucopyranoside (Galα3Galβ4GlcNAcβ—). This 3-aminopropylglycoside may be prepared according to Scheme 4.

The glycosyl acceptor (3-trifluoroacetamidopropyl)-2-acetamido-3-O-acetyl-6-O-benzyl-2-deoxy-4-O-(2,4-di-O-acetyl-6-O-benzyl-β-D-galactopyranosyl)-β-D-glucopyranoside (XXII) was prepared according to the method disclosed in the publication of Pazynina et al (2008). A mixture of the glycosyl acceptor (XXII) (500 mg, 0.59 mmol), thiogalactopyranoside (XXI) (576 mg, 1.18 mmol), NIS (267 mg, 1.18 mmol), anhydrous CH$_2$Cl$_2$ (25 ml) and molecular sieves 4 Å (500 mg) was stirred at −45° C. for 30 min under an atmosphere of Ar. A solution of TfOH (21 μl, 0.236 mmol) in anhydrous CH$_2$Cl$_2$ (0.5 ml) was then added. The reaction mixture was stirred for 2 h at −45° C. and the temperature was then increased to −20° C. over 4 h. The mixture was kept at −20° C. overnight. Then extra amounts of thiogalactopyranoside (XXI)(144 mg, 0.295 mmol), NIS (66 mg, 0.295 mmol) and TfOH (5 μl, 0.06 mmol) were added and the stirring maintained at −20° C. for 2 h before being allowed to slowly warm up to r.t. (1 h). A saturated aqueous solution of Na$_2$S$_2$O$_3$ was then added and the mixture filtered. The filtrate was diluted with CHCl$_3$ (300 ml), washed with H$_2$O (2×100 ml), dried by filtration through cotton wool, and concentrated. Gel filtration on LH-20 (CHCl$_3$-MeOH) afforded the product (XXIII) (600 mg, 80%), as a white foam.

$^1$H NMR (700 MHz, CDCl$_3$, characteristic signals), δ, ppm: 1.78-1.82 (m, 4H, CHCHC, OC(O)CH$_3$), 1.84-1.90 (m, 1H, CHCHC), 1.91, 1.94, 1.97, 1.98, 2.06 (5 s, 5×3H, 4 OC(O)CH$_3$, NH(O)CH$_3$), 3.23-3.30 (m, 1H, NCHH), 3.59-3.65 (m, 1H, NCHH), 4.05 (m, 1H, H-2$^I$), 4.33 (d, 1H, J$_{1,2}$ 7.55, H-1$^I$), 4.40 (d, 1H, J 12.04, PhCHH), 4.42 (d, 1H, J$_{1,2}$ 8.07, H-1$^{II}$), 4.45 (d, 1H, J 11.92, PhCHH), 4.48 (d, 1H, J 12.00, PhCHH), 4.50 (d, 1H, J 12.00, PhCHH), 4.52 (d, 1H, J 12.04, PhCHH), 4.54 (d, 1H, J 12.00, PhCHH), 4.57 (d, 1H, J 12.00, PhCHH), 4.64 (d, 1H, J 11.92, PhCHH), 4.99 (dd≈t, 1H, J 8.24, H-2$^{II}$), 5.08-5.13 (m, 2H, H-3$^I$, H-3$^{III}$) 5.23 (d, 1H, J$_{1,2}$ 3.31, H-1$^{III}$), 5.46 (d, 1H, J$_{3,4}$ 2.25, H-4$^{II}$), 5.54 (d, 1H, J$_{3,4}$ 3.11, H-4$^{III}$), 7.20-7.40 (m, 20H, ArH); 7.49-7.54 (m, 1H, NHC(O)CF$_3$). R$_f$ 0.4 (PhCH$_3$—AcOEt, 1:2).

The product (XXIII) (252 mg, 0.198 mmol) was deacetylated according to Zemplen (8 h, 40° C.), neutralized with AcOH and concentrated. The TLC (CH$_3$Cl-MeOH, 10:1) analysis of the obtained product showed two spots: the main spot with R$_f$ 0.45, and another one on the start line (ninhydrin positive spot) that was an indication of partial loss of trifluoroacetyl. Therefore, the product was N-trifluoroacetylated by treatment with CF$_3$COOMe (0.1 ml) and Et$_3$N (0.01 ml) in MeOH (10 ml) for 1 h, concentrated and subjected to column

SCHEME 4

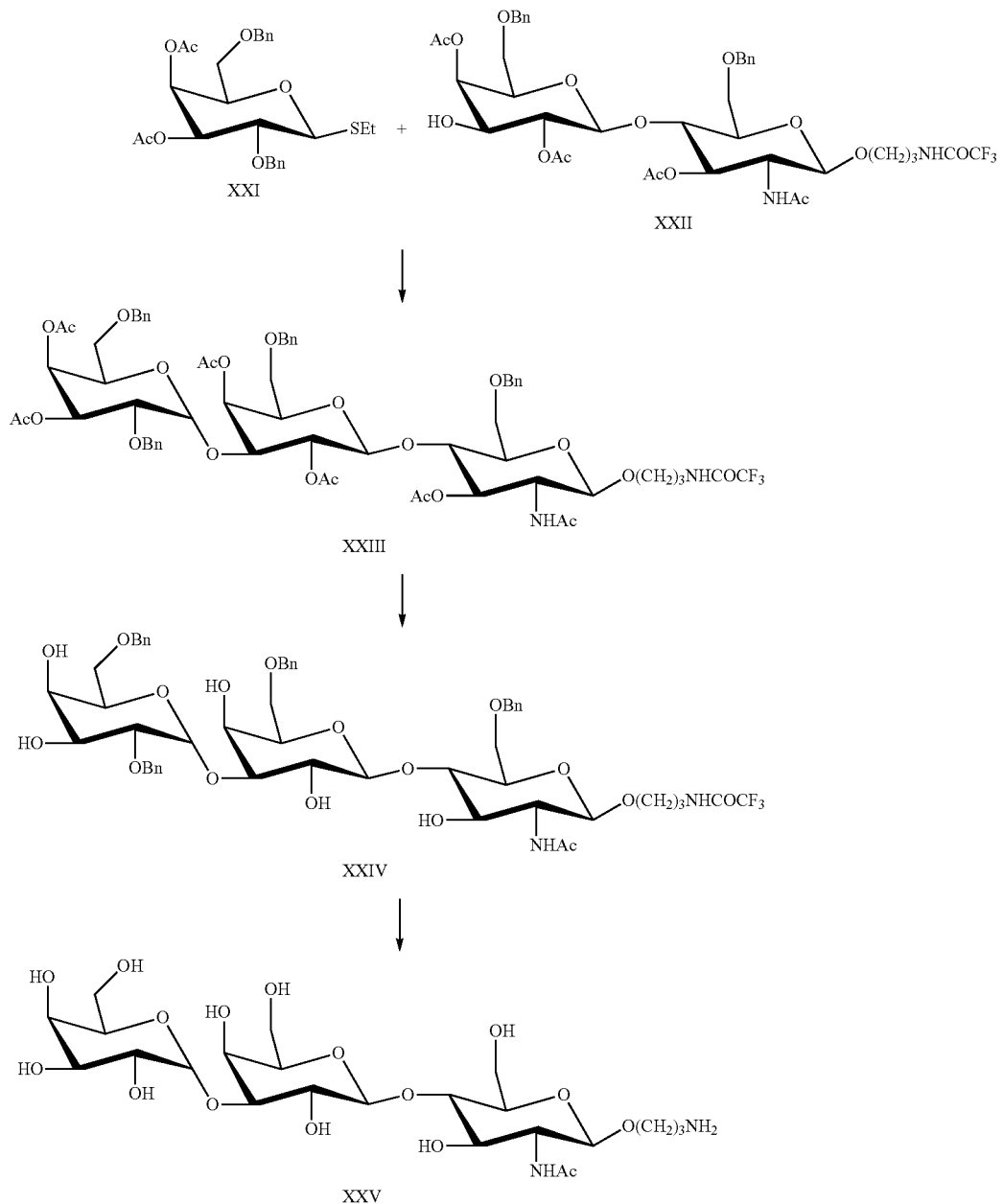

chromatography on silica gel (CHCl₃-MeOH, 15:1) to afford the product (XXIV) as a white foam (163 mg, 77%), $R_f$ 0.45 (CH₃Cl-MeOH, 10:1). The product (XXIV) was subjected to hydrogenolysis (200 mg Pd/C, 10 ml MeOH, 2 h), filtered, N-defluoroacetylated (5% Et₃N/H₂O, 3 h) and concentrated. Cation-exchange chromatography on Dowex 50×4-400 (H⁺) (elution with 5% aqueous ammonia) gave the product (XXV) (90 mg, 98%) as a white foam.

¹H NMR (D₂O, characteristic signals), δ, ppm: 1.94-1.98 (m, 2H, CCH₂C), 2.07 (s, 3H, NHC(O)CH₃), 3.11 (m, J 6.92, 2H, NCH₂), 4.54 and 4.56 (2d, 2H, $J_{1,2}$ 8.06, $J_{1,2}$ 7.87, H-1$^I$ and 5.16 (d, 1H, $J_{1,2}$ 3.87, H-1$^{III}$). $R_f$ 0.3 (EtOH-BuOH-Py-H₂O-AcOH; 100:10:10:10:3). Although the foregoing schemes are illustrated referencing the use of DSC the use of other homo-bifunctional cross-linkers such as disuc- cinimidylglutarate, disuccinimidyladipate and disuccinim- idylpimelate is also contemplated.

Biology

Ceramide Conjugates

Incorporation of a Ceramide Conjugates into Cell Membranes

Figure 3:
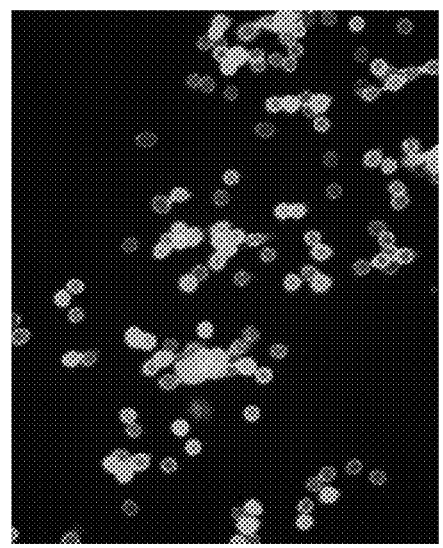
FIG. 3. Fluorescently labelled red blood blood cells modified by incorporation of the construct designated biotin-CMG(2)-Ad-DOPE from the publication of Bovin et al (2009) (A) or the ceramide conjugate where the functional moiety is biotin (X)(B).
Figure 3:
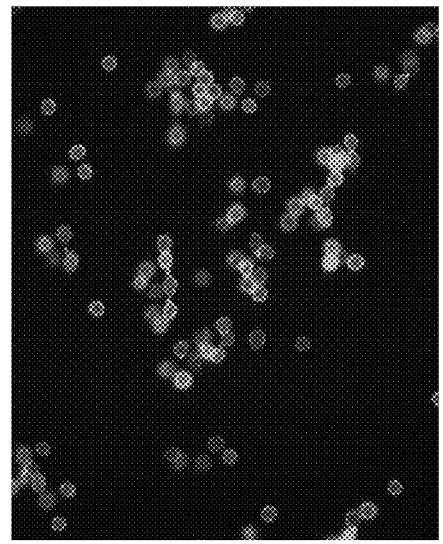
Figure 4:
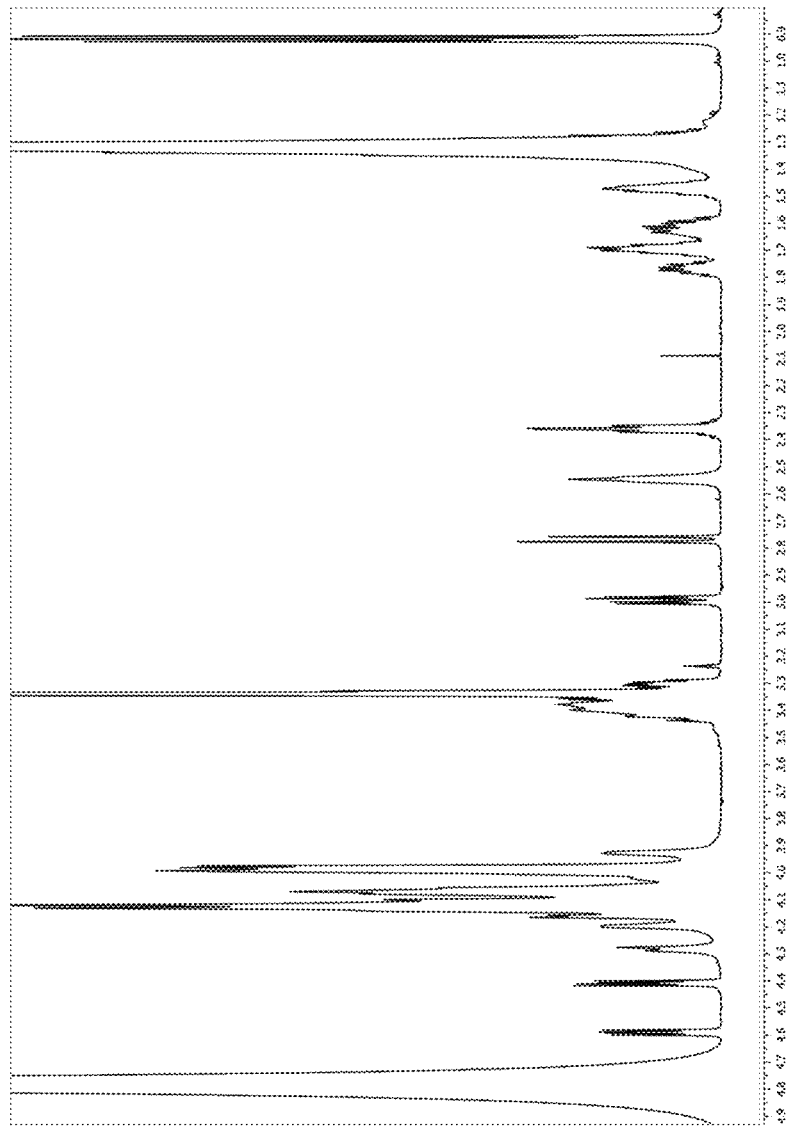
FIG. 4. $^1$H NMR spectrum of the sphingolipid analogue where the functional moiety is biotin (VI) (4 mg/mL in $[D_2]H_2O/[D_4]CH_3OH$ 1:1, 30° C., 700 MHz).
Figure 5:
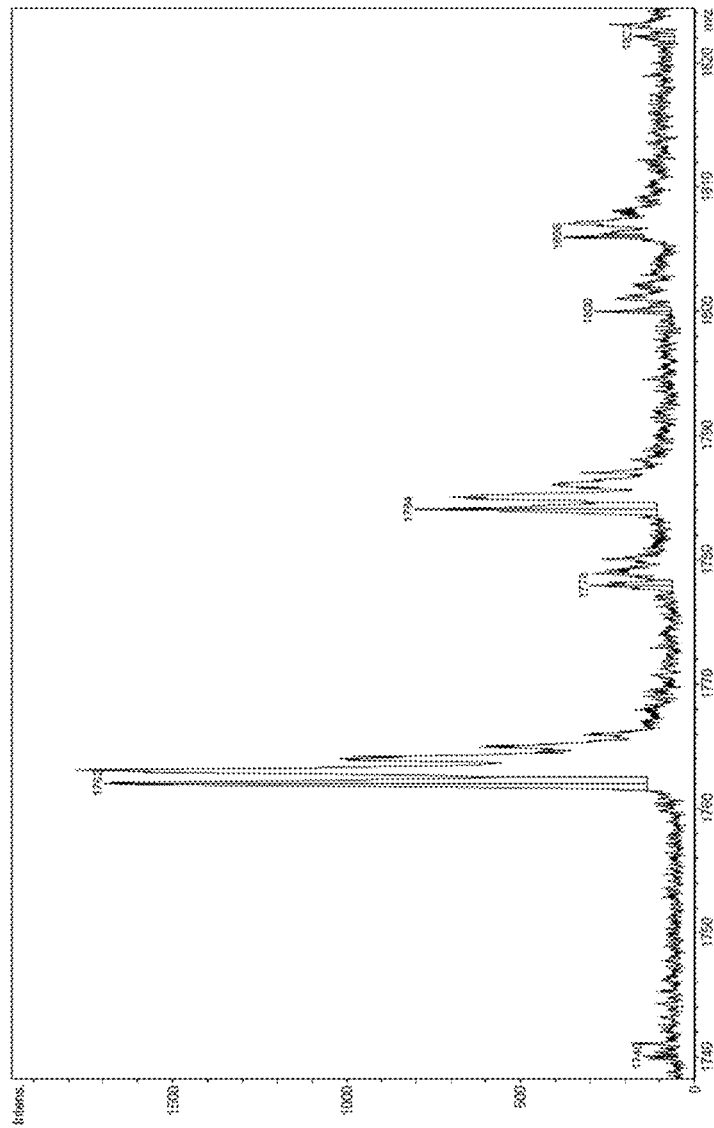
FIG. 5. MALDI TOF mass-spectrum of the sphingolipid analogue where the functional moiety is biotin (VI) ($C_{78}H_{131}N_{17}O_{25}S$, MW 1739). 1740: M+H; 1762; MNa+H; 1778: MK+H; 1784: MNa$_2$+H; 1800: MNaK+H; 1806: MNa$_3$+H; 1822: MKNa$_2$+H. Instrument: FLEX-PC, DHB matrix.
Figure 6:
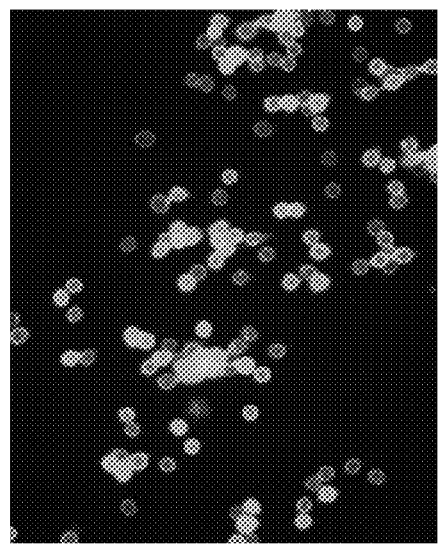
FIG. 6. Fluorescently labelled red blood blood cells modified by incorporation of the construct designated biotin-CMG(2)-Ad-DOPE from the publication of Bovin et al (2009) (A) or the sphingolipid analogue where the functional moiety is biotin (VI)(B).
Figure 6:
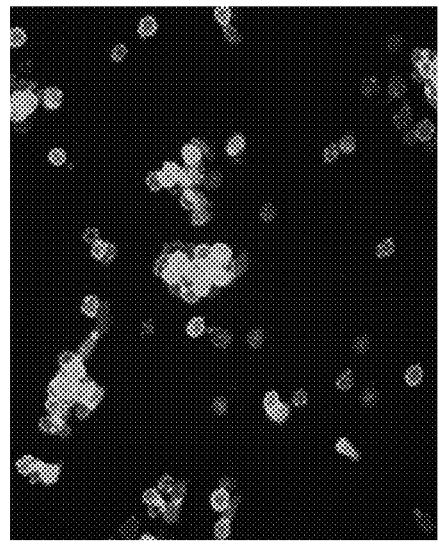

A 50 μL volume of packed red blood cells was re-suspended in an equal volume of a dispersion in phosphate buffered saline (PBS) (pH 7.2) of the ceramide conjugate (X). The re-suspended cells were incubated at 37° C. for two hours and then washed once with PBS. The modified cells were diluted with PBS to provide a suspension at a concentration equivalent to 5% of the packed cell volume. A 30 μL volume of the diluted suspension was then mixed with an equal volume of a 0.1 mg/mL solution of Avidin Alexa Flour™ 488 in PBS. The mixture was incubated at room temperature for 30 minutes before washing and re-suspending the modified cells in PBS. The fluorescence of cells in a 5 μL volume was observed using a microscope (Olympus BX51) at 400× magnification. Photomicrographs (1.903 seconds exposure time) are presented in FIG. 3.

The modified cells prepared using dispersions of the ceramide conjugate (X) at different concentrations (0 (control), 0.5, 5 and 50 μM) were scored. The results are presented in Table 1.

The observations form fluorescent labelling of the modified cells confirmed that both the ceramide conjugate (X) and the construct designated biotin-CMG(2)-Ad-DOPE spontaneously incorporated into cell membranes.

TABLE 1

Comparison of the fluorescence scores observed for red blood cells modified to incorporate either the ceramide conjugate (X) or the construct designated biotin-CMG (2)-Ad-DOPE from the publication of Bovin et al (2009).

| | Fluorescence score | |
|---|---|---|
| Concentration (μM) | ceramide conjugate | biotin-CMG (2)-Ad-DOPE |
| 0 | 0 | — |
| 0.5 | 0 to 1+ | 0 |
| 5 | 1+ | 2+ |
| 50 | 2 to 3+ | 3+ |

Derivatives of Sphingolipid Analogues

Incorporation of a Sphingolipid Analogue into Cell Membranes

A 50 μL volume of packed red blood cells was re-suspended in an equal volume of a dispersion in phosphate buffered saline (PBS) (pH 7.2) of the sphingolipid analogue (XVI). The re-suspended cells were incubated at 37° C. for two hours and then washed once with PBS. The modified cells were diluted with PBS to provide a suspension at a concentration equivalent to 5% of the packed cell volume. A 30 μL volume of the diluted suspension was then mixed with an equal volume of a 0.1 mg/mL solution of Avidin Alexa Flour™ 488 in PBS. The mixture was incubated at room temperature for 30 minutes before washing and re-suspending the modified cells in PBS. The fluorescence of cells in a 5 μL volume was observed using a microscope (Olympus BX51) at 400× magnification. Photomicrographs (1.903 seconds exposure time) are presented in FIG. 3.

The modified cells prepared using dispersions of the sphingolipid analogue (XVI) at different concentrations (0 (control), 0.5, 5 and 50 μM) were scored. The results are presented in Table 2.

Modified cells prepared using either the sphingolipid analogue (XVI) or the construct designated biotin-CMG(2)-Ad-DOPE from the publication of Bovin et al (2009) were indistinguishable.

Although the invention has been described with reference to embodiments or examples it should be appreciated that variations and modifications may be made to these embodiments or examples without departing from the scope of the invention. Where known equivalents exist to specific elements, features or integers, such equivalents are incorporated as if specifically referred to in this specification. Variations and modifications to the embodiments or

TABLE 2

Comparison of the fluorescence scores observed for red blood cells modified to incorporate either the sphingolipid analogue (XVI) or the construct designated biotin-CMG (2)-Ad-DOPE from the publication of Bovin et al (2009).

| | Fluorescence score | |
|---|---|---|
| Concentration (μM) | sphingolipid analogue | biotin-CMG (2)-Ad-DOPE |
| 0 | | |
| 0.5 | 0 | 0 |
| 5 | 2+ | 2+ |
| 50 | 3+ | 3+ | examples that include elements, features or integers disclosed in and selected from the referenced publications are within the scope of the invention unless specifically disclaimed. The advantages provided by the invention and discussed in the description may be provided in the alternative or in combination in these different embodiments of the invention.

REFERENCED PUBLICATIONS

Anderson et al (2014a) Conjugate compounds International application no. PCT/2013/000224 [Publ. no. WO 2014/088432 A1]

Anderson et al (2014b) Sphingoglycolipid analogues International application no. PCT/NZ2014/000113 [Publ. no. WO 2014/200363 A1]

Anderson et al (2015) Amino sphingoglycolipid analogues International application no. PCT/2015/050070 [Publ. no. WO 2015/187040 A1]

Bovin et al (2005) Synthetic membrane anchors International application no. PCT/NZ2005/000052 (publ. no. WO 2005/090368 A1).

Bovin et al (2009) Functional lipid constructs International application no. PCT/NZ2008/000266 (publ. no. WO 2009/0483434 A1).

Breusch, Friedrich L. (1954) *Isomeric and homologous series. VII. Homologous series* Chemische Berichte 87, 1051-6.

Choi et al (1996) Polyethylene glycol-modified ceramide lipids and liposome uses thereof International application no. PCT/CA1995/000556 (publ. no. WO 1996010391 A1).

Compton et al (2014) Organic compounds International application no. PCT/NZ2013/00133 [Publ.no. WO 2014/017928 A1]

Fukunaga et al (2003) *Synthesis of Lacto- and Neolacto-series Ganglioside Analogues Containing N-Glycolyl-neuraminic Acid: Probes for Investigation of Specific Receptor Structures Recognized by Influenza A Viruses* Journal of Carbohydrate Chemistry 22(9), 919-937.

Fuse et al (2006) *Synthesis and enzymatic susceptibility of a series of novel GM2 analogues* Glycoconjugate Journal 23(5/6), 329-343.

Galili (2010) Tumor lesion regression and conversion in situ into autologous tumor vaccines by compositions that result in anti-gal antibody binding U.S. Pat. No. 7,820,628 B2.

Hada et al (1999a) *Synthetic studies on glycosphingolipids from Protostomia phyla: synthesis of neogala-series glycolipid analogues containing a mannose residue from the earthworm Pheretima hilgendorfi* Chemical & Pharmaceutical Bulletin 47(9), 1265-1268.

Hada et al (1999b) *Synthetic studies on glycosphingolipids from the parasite Echinococcus multilocularis* Carbohydrate Research 316(1-4), 58-70.

Hada et al (2007) *Synthesis and biological activities of glycosphingolipid analogues from marine sponge Aplysinella rhax* Bioorganic & Medicinal Chemistry Letters 17(21), 5912-5915.

Hasegawa et al (1995) *Synthetic studies on sialoglycoconjugates. 70: Synthesis of sialyl and sulfo Lewis X analogues containing a ceramide or 2-(tetradecyl)hexadecyl residue* Journal of Carbohydrate Chemistry 14(3), 353-68.

Hasegawa et al (1996) *Synthetic studies on sialoglycoconjugates. 88. Synthesis of ganglioside GM3 and GM4 analogues containing 2- or 3-branched fatty-alkyl residues in place of ceramide* Journal of Carbohydrate Chemistry 15(5), 623-637.

Ikami et al (1997) *Synthetic studies on sialoglycoconjugates. 97. Synthetic studies on selectin ligands/inhibitors: one-pot synthesis of the mono- and oligo-sulfated 2-(tetradecyl)hexadecyl β-D-galacto- and lactopyranosides as the sulfatide mimetics* Journal of Carbohydrate Chemistry 16(6), 859-875.

Ikami et al (1998) *Synthetic studies on sialoglycoconjugates. CVII. Synthetic studies on selectin ligands/inhibitors. Synthesis and biological evaluation of sulfated and phosphorylated β-D-galacto- and lactopyranosides containing fatty-alkyl residues of different carbon chain lengths* Chemical & Pharmaceutical Bulletin 46(5), 797-806.

Ishida et al (1996) Glycolipid derivatives acting as ligands for selectins U.S. Pat. No. 5,589,465.

Ishida et al (1997) *Synthetic studies on sialoglycoconjugates. 98. Synthesis of the 3'-C-carboxymethyl Lewis X derivative: a novel selectin blocker* Carbohydrate Research 303(2), 131-133.

Kiso and Ishida (2003) Carboxymethylgalactose derivatives U.S. Pat. No. 6,503,885 B1.

Kiso et al (2011) Synthetic glycolipid-containing liposome U.S. patent application Ser. No. 12/918,467 (Publ. No. US 2011/0286937 A1).

Kryczka et al (2007) *Product class 15: glycosyl oxygen compounds (except di- and oligosaccharides* Science of Synthesis 29, 971-1055.

Ladisch and Hasegawa (1996) Synthetic glanglioside derivatives International Application No. PCT/US95/11670 (Publ. No. WO 9608257 A1).

Ladisch et al (1994) *A chemically synthesized sialic acid-containing glycoconjugate 2-(tetradecylhexadecyl)-O-(5-acetamido-3,5-dideoxy-D-glycero-α-D-galacto-2-nonulopyranosylonic acid)-(2→3)-O-β-D-galactopyrannosyl-(1→4)-β-D-glucopyrannoside, is a potentinhibitor of cellular immune responses* Biochemical and Biophysical Research Communications 203(2), 1102-9.

Ohira and Iida (2000) Lewis X derivatives U.S. Pat. No. 6,084,081.

Otsubo et al (2001) *Synthesis of novel ganglioside GM4 analogs containing N-deacetylated and lactamized sialic acid: probes for searching new ligand structures for human L-selectin* Carbohydrate Research 330(1), 1-5.

Otsubo et al (2001) *Synthetic studies of sialo-glyconjugates. Part 120. The first, efficient synthesis of novel SLex neoglycolipids containing N-deacetylated and lactamized sialic acid: key ligand structures for selectin binding* Journal of Carbohydrate Chemistry 20(3 & 4), 329-334.

Otsubo et al (2002) *An efficient and straightforward synthesis of sialyl Lex glycolipid as a potent selectin blocker* Journal of Carbohydrate Chemistry 21(3), 247-255.

Otsubo et al (2005) *Synthetic studies on sialoglycoconjugates. Part 137. Design and synthesis of a novel neoglycolipid containing sialyl Lewis X determinant carried on the mucin GlcNAcβ1-6GalNAcα core structure* Tetrahedron: Asymmetry 16(7), 1321-1327.

Pazynina et al (2008) *The synthesis of linear trilactosamine* Russian Journal of Bioorganic Chemistry, Vol. 34, No. 5, 625-631.

Tanahashi et al (1997) *Synthetic studies on sialoglyconjugates. 96. Synthetic studies on selectin ligands/inhibitors: a systematic synthesis of sulfatide and its higher congeners carrying 2-(tetradecyl)hexadecyl group as a ceramide substitute* Journal of Carbohydrate Chemistry 16(6), 831-858.

Terada et al (1998) *Synthetic studies on sialoglycoconjugates. 104: Synthesis of EDN-Lewis X ganglioside analogues containing modified reducing terminal and L-rhamnose in place of L-fucose* Journal of Carbohydrate Chemistry 17(4&5), 519-534.

Tsukida et al (1997) *A Highly Practical Synthesis of Sulfated Lewis X: One-Pot, Two-Step Glycosylation Using "Armed/Disarmed" Coupling and Selective Benzoylation and Sulfation* Journal of Organic Chemistry 62(20), 6876-6881

Ulusoy, Emin (1954) *Preparation of the symmetrical 2,2'-dialkylethanols from C22H46O to C32H66O* Istanbul Universitesi Fen Fakultesi Mecmuasi, Seri C:[Astronomi-Fizik-Kimya] 19, 169-70.

Wada et al (1996) *Studies on Selectin Blockers. 2. Novel Selectin Blocker as Potential Therapeutics for Inflammatory Disorders* Journal of Medicinal Chemistry 39(10), 2055-9.

Wilhelm et al (1995) *Synthesis of glycolipids as membrane-bound stabilizing carbohydrates* Liebigs Annalen (9), 1673-9.

Yamaguchi et al (2005) *6-O-Sulfo sialyl-p-globoside and sialyl Lewis X neo-glycolipids containing lactamized neuraminic acid: Synthesis and antigenic reactivity against G159 monoclonal antibody* Glycoconjugate Journal 22(3), 95-108.

Yoon et al (2007) *Self-recognition of N-linked glycans with multivalent GlcNAc, determined as ceramide mimetic conjugate* Glycobiology 17(9), 1007-1014.

Yoshida et al (1996) *Synthetic studies on sialoglycoconjugates. 85: Synthesis of sialyl Lewis X ganglioside analogues containing a variety of anionic substituents in place of sialic acid* Journal of Carbohydrate Chemistry 15(4), 399-418.

Zhang et al (1999) *Synthetic studies on sialoglycoconjugates. 108. Chemoenzymic synthesis of ganglioside GM4 analogues as potential immunosuppressive agents* Journal of Carbohydrate Chemistry 18(2), 225-239.

The invention claimed is:
1. A 2-branched fatty alkyl derivative of the structure:

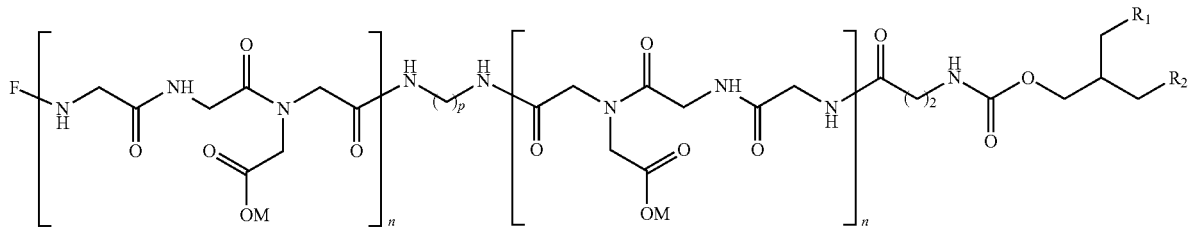

where F is H or comprises a functional moiety, M is a monovalent cation, n is the integer 1, 2, 3 or 4, p is the integer 1, 2 or 3, and $R_1$ and $R_2$ are independently selected from the group consisting of $C_{11-15}$ alkyl.

2. The derivative of claim 1 where F is a functional moiety selected from the group consisting of:

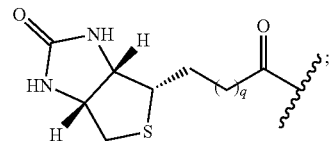

-continued

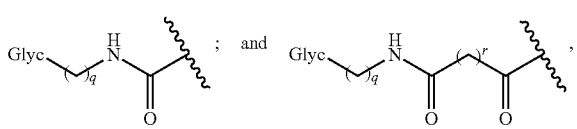

where q is the integer 2, 3 or 4, r is the integer 3, 4 or 5 and Glyc is a mono-, di-, tri- or oligosaccharide linked via a glycosidic bond.

3. The derivative of claim 2 of the structure:

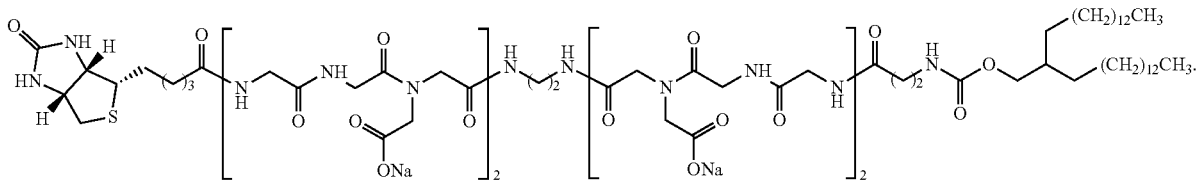

4. The derivative of claim 2 of the structure:

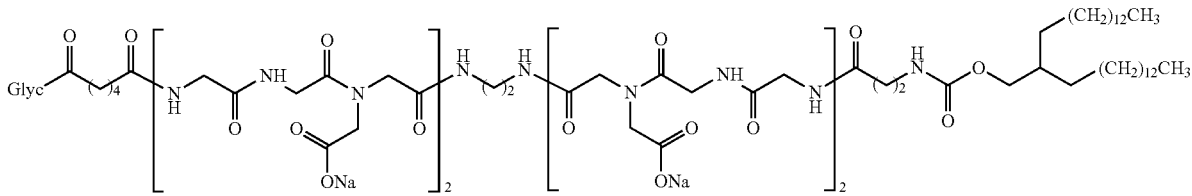

where Glyc is an aminoalkyltrisaccharide.

5. The derivative of claim 4 where the aminoalkyltrisaccharide is of the structure:

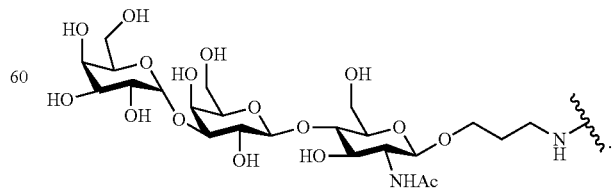

* * * * *